United States Patent
Mitrophanous et al.

(10) Patent No.: US 7,351,585 B2
(45) Date of Patent: Apr. 1, 2008

(54) RETROVIRAL VECTOR

(75) Inventors: Kyriacos Mitrophanous, Oxford (GB); Mary Collins, London (GB); Yasuhiro Takeuchi, London (GB); Yasuhiro Ikeda, London (GB)

(73) Assignee: Oxford Biomedica (UK) Ltd., Oxford (GB)

( * ) Notice: Subject to any disclaimer, the term of this patent is extended or adjusted under 35 U.S.C. 154(b) by 0 days.

(21) Appl. No.: 10/654,537

(22) Filed: Sep. 2, 2003

(65) Prior Publication Data

US 2006/0258006 A1    Nov. 16, 2006

Related U.S. Application Data

(60) Provisional application No. 60/417,673, filed on Oct. 9, 2002.

(30) Foreign Application Priority Data

Sep. 3, 2002    (GB) ................................ 0220467.5

(51) Int. Cl.
  *C12N 5/10*      (2006.01)
  *C12N 15/48*     (2006.01)
  *C12N 15/49*     (2006.01)
  *C12N 15/63*     (2006.01)
  *C12N 15/64*     (2006.01)
  *C12N 15/867*    (2006.01)
  *A61K 48/00*     (2006.01)

(52) U.S. Cl. .................... 435/455; 435/325; 435/320.1; 435/366

(58) Field of Classification Search ................ None
See application file for complete search history.

(56) References Cited

U.S. PATENT DOCUMENTS 5,691,177 A * 11/1997 Guber et al. ................. 435/456
6,312,683 B1   11/2001 Kingsman et al.
6,392,015 B1 *  5/2002 Panganiban et al. ......... 530/350
6,852,530 B2 *  2/2005 Silver et al. ................. 435/325
6,969,598 B2 * 11/2005 Olsen et al. ................. 435/69.1
6,995,009 B1 *  2/2006 Kitamura et al. ......... 435/320.1

FOREIGN PATENT DOCUMENTS

| | | |
|---|---|---|
| EP | 1059357 A1 | 12/2000 |
| GB | 2337520 A | 11/1999 |
| WO | WO 98/42856 | 10/1998 |
| WO | WO 98/46778 | 10/1998 |
| WO | WO 99/32646 | 7/1999 |

OTHER PUBLICATIONS

Ikeda, Yasuhiro, et al., "Continuous high-titer HIV-1 vector production", *nature biotechnology*, 2003, 21:569-572.

Farson, Deborah, et al., "A New-Generation Stable Inducible Packaging Cell Line for Lentiviral Vectors", *Human Gene Therapy*, (2001) 12:981-997.

Demaison, Christophe, et al., "High-Level Trasduction and Gene Expression in Hematopoietic Repopulating Cells Using a Human Immunodeficiency Virus Type 1-Based Lentiviral Vector Containing an Internal Spleen Focus Forming Virus Promoter", *Human Gene Therapy*, (2002) 13:803-813.

Kung, Sam K. P., et al., "A Murine Leukemia Virus (MuLV) Long Terminal Repeated Derived from Rhesis Macaques in the Context of a Lentivirus Vector and MuLV gag Sequence Results in High-Level Gene Expression in Human T. Lymphocytes", *Journal of Virology*, (2000) 74/8: 3668-3681.

Olsen, John C., "EIAV, CAEV and Other Lentivirus Vector Systems", *Somatic Cell and Molecular Genetics* (2000) 26/1-6:131-145.

* cited by examiner

*Primary Examiner*—David Guzo
(74) *Attorney, Agent, or Firm*—Frommer Lawrence & Haug LLP; Thomas J. Kowalski; Anne-Marie C. Yvon

(57) ABSTRACT

Provided herein is a retroviral vector comprising, and capable of expressing, a nucleotide of interest (NOI), wherein the NOI encodes an RNA or protein which is harmful to a cell.

14 Claims, 19 Drawing Sheets

|  | CNC-GPRT | | CNC-SYNGP | |
|---|---|---|---|---|
|  | Transfection | Infection | Transfection | Infection |
| HeLa | 2/324 | 12/228 | 0/44 | 17/28 |
| HT1080 | 0/83 | 0/72 | 0/20 | 71/75 |
| 293T (no selection) | N/A | 1/128 | N/A | 92/108 |

Figure 2

HeLa
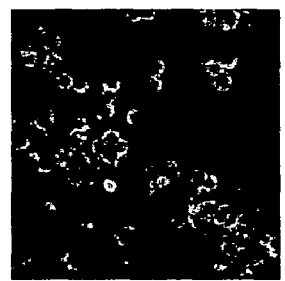
CNC-SYNGP (SYNGP1, infection)
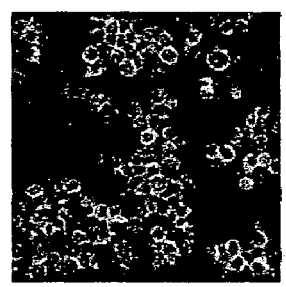
CNC-GPRT (GPRT1, infection)
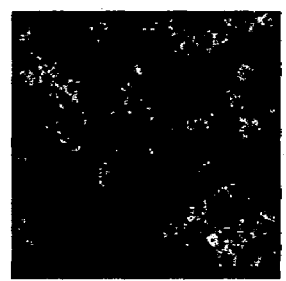
CNC-GPRT (TF1, Transfection)
Parental
Figure 3

Figure 8

| | 293TGPRT1+R1 Ampho | HT-STAR Ampho | STAR Ampho | STAR RDpro | STAR GALV+ |
|---|---|---|---|---|---|
| H7G infection (MOI = 10) | $1.2 \times 10^6$ | $4.4 \times 10^6$ | $1.4 \times 10^7$ | $7.6 \times 10^6$ | N/D |
| HV infection (MOI = 10) | $2.3 \times 10^5$ ($4.3 \times 10^4 \sim 6.1 \times 10^6$, n=8) | $1.3 \times 10^6$ | $1.2 \times 10^7$ ($4.5 \times 10^6 \sim 5.1 \times 10^7$, n=9) | $8.5 \times 10^6$ ($1.6 \times 10^6 \sim 8.3 \times 10^7$, n=9) | $1.6 \times 10^6$ |
| HV infection (MOI = 2) | N/D | $8.0 \times 10^5$ | $8.5 \times 10^6$ | $4.1 \times 10^6$ | $1.7 \times 10^6$ |
| pHV + pPuro transfection/selection | N/D | N/D | $2.9 \times 10^5$ ($2.6 \times 10^4 \sim 2.3 \times 10^6$, n=12) | N/D | N/D |
| pSIN-CSGW + pPuro transfection/selection | N/D | N/D | $3.5 \times 10^5$ ($6.2 \times 10^4 \sim 1.2 \times 10^7$, n=11) | N/D | N/D |

Figure 9

| | 10 | 27 | 49 | 70 | 102 | 270 | (days p.i.) |
|---|---|---|---|---|---|---|---|
| STAR Ampho HV (MOI 10) | $8.8 \times 10^6$ | $1.2 \times 10^7$ | $8.2 \times 10^6$ | $1.1 \times 10^7$ | $1.1 \times 10^7$ | ND | |
| STAR RDpro HV (MOI 10) | $6.3 \times 10^6$ | $3.5 \times 10^6$ | $6.2 \times 10^6$ | $8.2 \times 10^6$ | $5.8 \times 10^6$ | ND | |
| 293TGPRT1+R1-Ampho-HV#1 | ND | $6.1 \times 10^6$ | ND | $4.8 \times 10^6$ | $6.2 \times 10^6$ | $5.5 \times 10^6$ | |

Figure 10

| Gag-Pol-Rev / Vector / Env | 3 | 7 | 14 days p.i. |
|---|---|---|---|
| Transient | | | |
| pCMVR8.91 / pHV / pMD-G | 412, 322, ND | 360, 78, 785 | 48, 21, ND |
| pCMVR8.91 / pHRSIN-puro / pMD-G | | 125 | |
| pCMVR8.91 / pHV/ phCMV-RDpro | | 145, 420, 60 | 22, 38, ND |
| pSYNGP, pCNC-Rev/ pHV/ pMD-G | | 16, 0 | 8, 0 |
| pSYNGP, pCNC-Rev / pHV / phCMV-RDpro | | 11, 0, 2 | 0, 2, ND |
| Stable | | | |
| 293TGPRTi+Rii -HV#1 / pMD-G (transient) | 7, 79, ND | 16, 52, 36 | 0, 7, ND |
| STAR/ HV#1/ RDpro | 14, 0, 0 | 4, 0, 0 | 0, 0, ND |

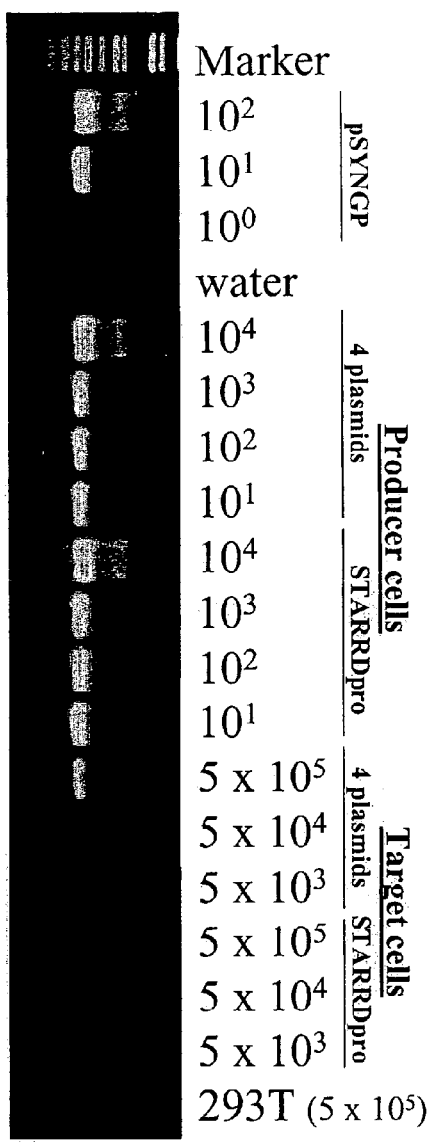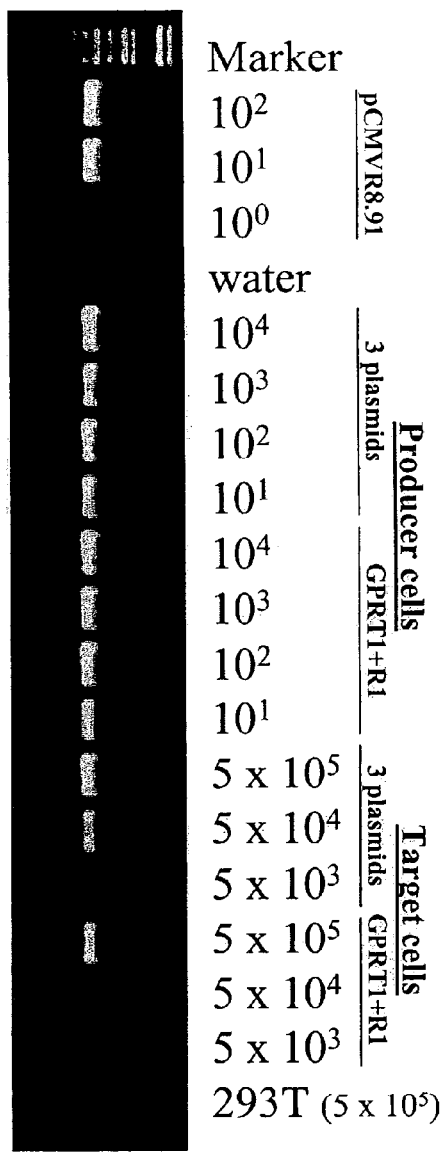
Figure 11

Figure 19
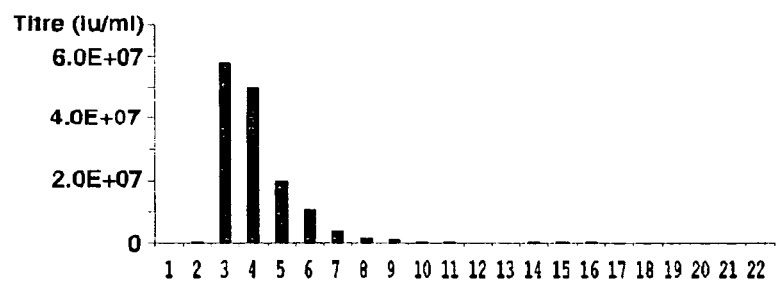
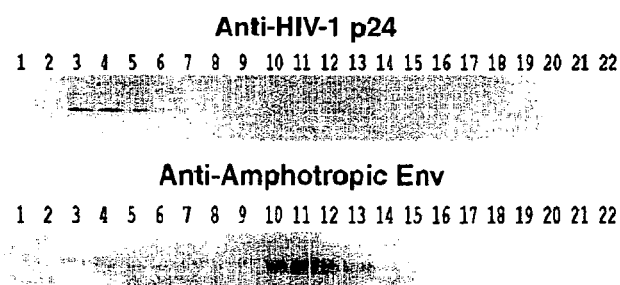
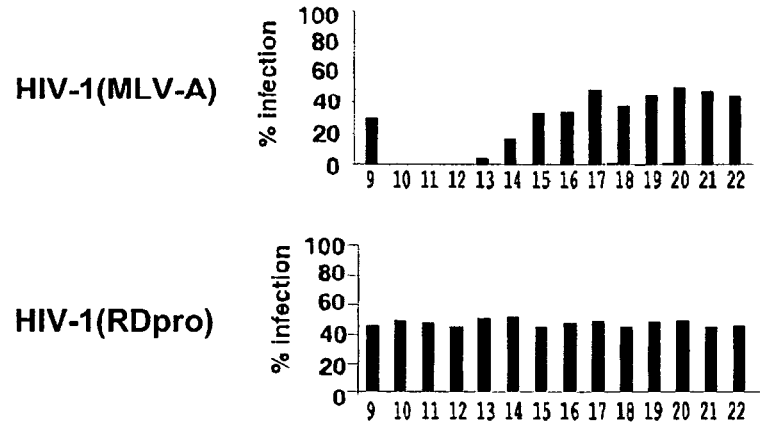

RETROVIRAL VECTOR

RELATED APPLICATIONS

This application is related to U.S. Provisional Patent Application No. 60/417,673 filed Oct. 9, 2002 and GB 0220467.5 filed Sep. 3, 2002, each of which is incorporated herein by reference in its entirety.

FIELD OF THE INVENTION

The present invention relates to a retroviral vector, and particularly, but not exclusively, to a novel system for engineering cells to produce recombinant RNAs or proteins which are potentially harmful to the cells. The present invention also relates to a retroviral vector which is itself capable of expressing a retroviral particle that is capable of delivering a nucleotide sequence of interest (hereinafter abbreviated to "NOI")—or even a plurality of NOIs—to a site of interest. More particularly, the present invention relates to vectors, stable cell lines and methods useful in gene therapy.

BACKGROUND

Gene therapy includes any one or more of: the addition, the replacement, the deletion, the supplementation, the manipulation etc. of one or more nucleotide sequences in, for example, one or more targeted sites—such as targeted cells. If the targeted sites are targeted cells, then the cells may be part of a tissue or an organ. General teachings on gene therapy may be found in Molecular Biology.

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favourable phenotype; cells can be manipulated at the molecular level to treat cancer or other conditions—such as immune, cardiovascular, neurological, inflammatory or infectious disorders; antigens can be manipulated and/or introduced to elicit an immune response—such as genetic vaccination.

In recent years, retroviruses have been proposed for use in gene therapy. Essentially, retroviruses are RNA viruses with a life cycle different to that of lytic viruses. In this regard, when a retrovirus infects a cell, its genome is converted to a DNA form. In other words, a retrovirus is an infectious entity that replicates through a DNA intermediate. More details on retroviral infection etc., are presented later on.

As mentioned above, retroviruses have been proposed as a delivery system (otherwise known as a delivery vehicle or delivery vector) for inter alia the transfer of a NOI, or a plurality of NOIs, to one or more sites of interest. The transfer can occur in vitro, ex viva, in viva, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging.

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome, but wherein the modified viral genome is unable to propagate itself due to a lack of structural proteins. When integrated in the host genome, expression of the NOI occurs—resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest—such as a targeted cell or a targeted cell population.

It is possible to propagate and isolate retroviral vectors (e.g., to prepare suitable titres of the retroviral vector) for subsequent transduction of, for example, a site of interest by using a combination of a packaging or helper cell line and a recombinant vector.

In some instances, propagation and isolation may entail isolation of the retroviral gag, pol and env genes and their separate introduction into a host cell to produce a "packaging cell line". The packaging cell line produces the proteins required for packaging retroviral RNA. However, when a recombinant vector carrying a NOI and a psi region is introduced into the packaging cell line, the helper proteins can package the psi-positive recombinant vector to produce the recombinant virus stock. This is commonly known as a "producer cell". The vector can be used to infect cells to introduce the NOI into the genome of the cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses".

The design of retroviral packaging cell lines has evolved to address the problem of inter alia the spontaneous production of helper virus that was frequently encountered with early designs. As recombination is greatly facilitated by homology, reducing or eliminating homology between the vector and gag/pol has reduced the problem of helper virus production.

More recently, packaging cells have been developed in which the gag/pol and env viral coding regions and the viral vector are carried on separate expression plasmids that are independently transfected into a packaging cell line so that three recombinant events are required for wild type viral production.

Transient transfection can be used to make vectors. In this regard, transient transfection has been used if the vector or retroviral packaging components are toxic to cells. Components typically used to generate retroviral vectors include a plasmid encoding the Gag/Pol proteins, a plasmid encoding the env protein and a plasmid containing a NOI. Vector production involves transient transfection of one or more of these components into cells containing the other required components. If the vector encodes toxic genes or genes that interfere with the replication of the host cell, such as inhibitors of the cell cycle or genes that induce apoptosis, it has proved difficult to generate stable vector-producing cell lines, thus transient transfection can be used to produce the vector before the cells die. However, the aforementioned technique can be problematic in the sense that the titre levels are not always satisfactory, it is difficult to make large batches of virus, and safety tests must be performed on each small batch.

In view of the toxicity of some HIV proteins, e.g., the HIV protease—which can make it difficult to generate stable HIV-based packaging cells—HIV vectors are usually made by transient transfection of vector and helper virus. Some workers have even replaced the HIV env protein with that of vesicular stomatis virus (VSV). A drawback, however, with this approach is that the VSV-G protein is quite toxic to cells.

Thus, and as indicated, retroviral vectors are used extensively in biomedical research and for gene therapy. Current methods for the production of retroviral vectors make use of the fact that the two roles of the wild-type retrovirus genome, that is protein encoding and as a template for new genome copies, can be de-coupled. Protein that is required for the assembly of new virus particles and for enzyme and regulatory functions can be produced by non-genome sequences in, for example, a mammalian packaging cell line. A genome sequence lacking the protein encoding functions is provided, so that the resulting retroviral vector particles are capable of infecting but not of replicating in a target cell. The genome sequence can also be designed for delivery and integration of a therapeutic gene. Standard methods for producing murine leukaemia virus (MLV)-based vectors, for example, include use of stably engineered cell lines expressing the gag-pol and env genes (the packaging components) of MLV. These will package a compatible retroviral vector genome introduced by transfection with an appropriate plasmid. An alternative method for producing HIV based vectors, for example, involves simultaneous transient transfection of gag-pol, env, and vector genome plasmids into suitable cells.

Although the principles of these systems are well understood, in practice the re-constructed virus assembly system often fails to generate the quantity of vector particles required in practice for use in gene therapy. Retroviral vector particles are generally harvested by removing supernatant from a culture of particle-producing cells. The resulting suspension may be concentrated with respect to the vector particles, using physical methods, but only to a limited degree as problems such as aggregation and damage tend to arise. Thus, it may only be possible to concentrate a suspension of vector particles by up to 100-fold.

The same issues arise when trying to produce a recombinant protein which is potentially harmful to the host cell in which it is being expressed. One approach that has been considered is to use an inducible system; however, this does not overcome the basic problem of toxicity, inducible production is only transient and problems have arisen from "leaky" promoters.

Vectors based on human immunodeficiency virus type 1 (HIV-1) offer a means for the delivery of therapeutic transgenes into a wide variety of cell types, both dividing and non-dividing. HIV-1 based vectors have commonly been produced either transiently or using packaging cell lines in which vector production is induced. Until recently no stable packaging cells to continuously produce high titre HIV-1 vectors were available, because it had been difficult to stably express large amounts of HIV-1 gag-pol. Furthermore, it has also proven to be difficult to continuously produce the rhabdovirus vesicular stomatitis virus G protein (VSV-G), which is most commonly used to replace HIV-1's own envelope proteins and 'pseudotype' HIV-1 vector particles.

SUMMARY OF THE INVENTION

The present invention provides an improved system for preparing viral particles that may be of subsequent use in medicine. In particular, the present invention provides an improved system for preparing a continuous supply of recombinant proteins and/or viral particles that may be of subsequent use in medicine. The present invention also provides an improved system for preparing a high titre of recombinant proteins and/or viral particles that may be of subsequent use in medicine. Thus, a stable, constitutive packaging system has been developed. This system rapidly and reproducibly generates large batches of high titre vectors, which allows, e.g., extensive control tests, an important aspect for clinical use.

According to one aspect of the present invention, there is provided a method for generating cell lines which result in stable, high level expression of HIV proteins. In more detail, it has been discovered that retroviral infection can result in stable HIV gag-pol expression. More generally, it has been discovered that the concept of retroviral gene delivery may be used to stably express other somewhat cytotoxic proteins.

According to another aspect of the present invention there is provided a composition in the form of a retroviral vector (a first retroviral vector) comprising, and capable of expressing, a nucleotide of interest (NOI), wherein the NOI encodes an RNA or protein which is potentially harmful to a cell. The retroviral vector will be capable of infecting a cell.

The term "potentially harmful to a cell" includes a protein that is capable of altering the metabolic processes or possessing a destructive action on cells, i.e., is potentially cytotoxic. Protein toxicity can manifest itself on different levels, e.g., some proteins inhibit cell growth, whereas other proteins also kill them. Some proteins interfere with replication of the host cell, such as inhibitors of the cell cycle or proteins that induce apoptosis. It has been found that the present invention is particularly useful in the production of proteins which show some degree of detrimental effect to the cell, inhibit the cell function at sublethal levels. Whether a protein is harmful to a cell is normally assessed by expressing the protein in a cell using a constitutive promoter and determining whether there is any harmful effect on the cell compared to a control.

In one aspect the NOI is capable of expressing an HIV protein, such as HIV protease. Preferably the NOI is useful in medicine, e.g., cancer therapy. The NOI often is present in the retroviral vector within a transcription unit. In one aspect the NOI may form part of a second retroviral genome, which may itself contain a second NOI. This second NOI is preferably useful in medicine e.g., gene therapy. This second NOI may or may not be harmful to a cell.

Thus, a particular advantage of the present invention is that it allows the production of a packaging cell line that produces retroviral particles, including pseudotyped particles, at a higher titre than conventional packaging cell lines, and produces such retroviral particles for a longer period. This advantage is achieved through stable integration of at least one component of the retroviral particle, which component is capable of being integrated into the cell's genome through infection by a first retroviral vector. In this situation the NOI can be seen as encoding at least one component of a second retroviral particle.

Thus, according to this aspect of the present invention there is provided a composition in the form of a retroviral expression system comprising a first retroviral vector which comprises a second retroviral component, wherein the first retroviral vector is capable of infecting a cell and the second retroviral component encodes at least one component of a second retroviral vector. In other words, there is provided a retroviral expression system comprising a first retroviral vector which is capable of infecting a cell and which first retroviral vector encodes at least one component of a second retroviral vector, i.e., the second retroviral component is incorporated within the first retroviral vector. The term "capable of infecting a cell" refers to the first retroviral component is capable of integrating itself into the genome of a cell. The cell may be, or be used to form, a packaging or producer cell for production of the retroviral particle. For ease, the cell infected by the first retroviral vector sometimes is referred to as the "host cell".

In an embodiment of this system, cells may be transduced with a first retroviral component which comprises a polynucleotide sequence coding for a gene, such as gag-pol of the second retroviral component. Regulatory proteins, e.g., from the second retroviral particle, such as Tat and Rev, may be introduced for efficient vector genome production, along with env and the vector genome of the second retroviral component, resulting in the production of the second retroviral particle.

The second retroviral component may comprise the retroviral gag-pol gene or env. Contrary to the prejudice in the art we have found that the toxicity of e.g., gag-pol gene and env is reduced when stably expressed following integration using a retroviral vector. Preferably the first retroviral component is derivable from a different retrovirus to the second retroviral component. Preferably the first retroviral component is derived from MLV. Preferably the second retroviral vector component is derived from HIV or EIAV, more preferably HIV, even more preferably HIV-1.

In other embodiments of the invention there is provided: a retroviral vector according to the present invention in the form of an integrated provirus; a retroviral production system for producing the retroviral vector of the present invention comprising a nucleic acid sequence encoding for the first viral vector component and a nucleic acid sequence encoding for the second viral vector component; a retroviral vector produced by the production system of the present invention; a retroviral particle obtained from the retroviral vector or production system of the present invention; a cell infected with the retroviral vector and wherein the NOI encodes a protein which is harmful to said cell; a retroviral vector, a retroviral particle, or a cell of the present invention for use in medicine; a method of using a retroviral vector, a retroviral particle, or a cell of the present invention to produce a protein which is harmful to a cell; a method of using a retroviral vector, a retroviral particle or a cell of the present invention to deliver an NOI to a patient in need of same; a method of producing a stable cell line comprising infecting a cell with a retroviral vector or a retroviral particle of the present invention; and a method of producing a protein which is harmful to a cell comprising infecting the cell with a retroviral vector or a retroviral particle of the present invention.

The present invention allows expression of recombinant proteins which may be harmful to a cell line, and have therefore proved difficult to produce using conventional approaches. The present invention allows expression which is stable, long-term, and high level. The term "long term" includes expression over periods of at least 3 months. The term "high level" include levels of HIV-1 p24 secretion up to about 850 ng/ml and recombinant HIV-1 viral titres up to $10^7$ 293T infectious units/ml. The present invention thus allows the production of cell lines which continuously produce vectors, such as HIV-1 based vectors, and proteins of interest, and allows the reproducibly generation of large batches of these products for pre-clinical and clinical use. Whilst not wishing to be bound by any theory, it is believed that introduction of coding regions, such as the HIV-1 gag-pol coding region, by retroviral infection results in the stable, high level expression of proteins such as can occur following retroviral infection.

BRIEF DESCRIPTION OF THE DRAWINGS

FIG. 1A illustrates pCNC-MCS. FIG. 1B illustrates pCNC-GPRT. FIG. 1C illustrates pCNC-SYNGP.

FIG. 2 is a table showing a comparison between transfection and retroviral transduction. G418-resistant clones were isolated 2 to 3 weeks after transfection or retroviral transduction, or 293T clones were isolated by limiting dilution after transduction, then screened for HIV p24 CA antigen expression by immunostaining.

FIG. 3 shows the results of an immunofluoresence assay for p24 expression in the HeLa clones. All twelve positive clones generated by CNC-GPRT transduction (designated HeLa CNC-GPRT clones) showed brighter fluorescence than the rare positive clones generated by transfection of pCNC-GPRT (designated HeLa TF clones).

FIG. 7A illustrates the pH7G vector which expresses Rev. FIG. 7B illustrates pHRSIN-CSGW. FIG. 7C illustrates pHV.

FIG. 8 is a table illustrating vector production from retroviral envelope-stable packaging cell lines. The packaging cells were infected with the H7G of HV vector or selected with puromycin after co-transfection of the vector and puromycin-resistance plasmids. Titres were determined on 293 T cells.

FIG. 9 is a table illustrating the level of viral production by STAR cells after prolonged culture.

FIG. 10 is a table illustrating the level of gag/pol functional transfer, measured by ability to rescue virus from VAT-7 cells which contain pH7G, Tat and ampho envelope. The numbers shown represent titre of rescued virus on 293 T cells.

FIG. 11 shows level of gag sequence transfer to 293 T cells measured by nested PCR.

FIGS. 19A-19C show graphs illustrating gel filtration analysis of HIV (MLV-A) preparation by centrifugal filtration. HIV-1 (MLV-A) pseudotypes were harvested in OptiMEM and subjected to concentration by centrifugal filtration. The resulting concentrated stock was fractionated by Sepharose gel filtration. Aliquots of each fraction were analysed for eGFP transduction (FIG. 19A) and the presence of HIV-1 CA and MLV-A env by Western blot using antibodies against CA and env gp70 (FIG. 19B). Aliquots from fractions 9-22 were mixed with fixed doses of either HIV (MLV-A) or HIV (RDpro) and then plated onto 293 T cells in the presence of 8 µg/ml polybrene. Percent eGFP transduction was measured by FACS (FIG. 19C).

DETAILED DESCRIPTION

Figure 1:
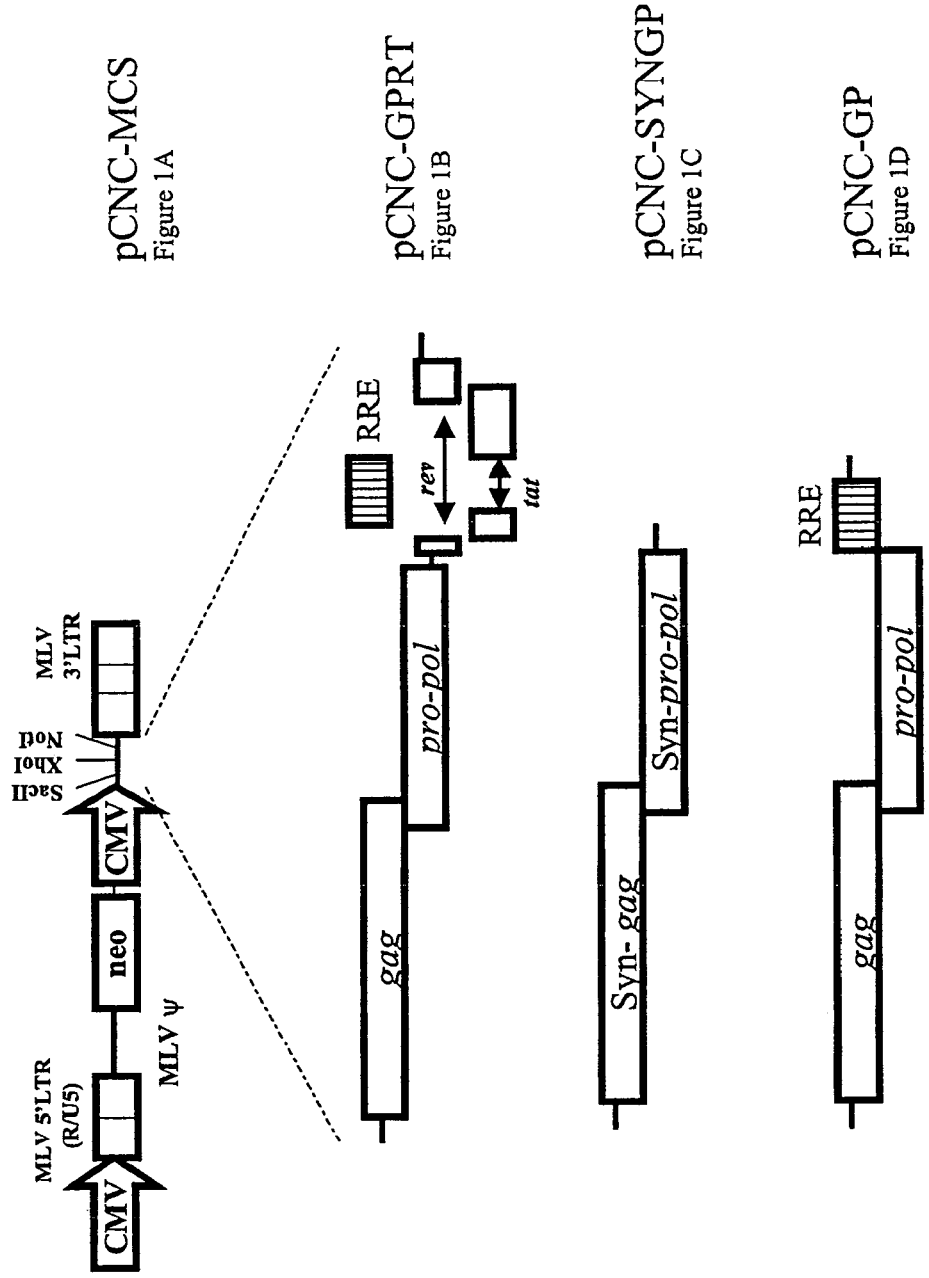
FIGS. 1A-1C show representations of MLV-based vector constructs. HIV gag-pol sequences were introduced into the cloning sites of pCNC-MCS to construct pCNC-GPRT, pCNC-SYNGP, and pCNC-GP. In more detail
FIG. 1D illustrates pCNC-GP.

Various preferred features and embodiments of the present invention will now be described by way of non-limiting example. Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc (as well as the complete version Current Protocols in Molecular Biology).

Retroviral Vector

The retroviral vector of the present invention can be seen as being in the form of a hybrid viral vector system which comprises primary viral vectors which encode a second or secondary viral vector, the first or primary vector being capable of infecting a host cell and of expressing therein the secondary viral vector, which secondary vector is capable of transducing a further target cell.

Thus a genetic vector of the invention consists of a primary vector manufactured in vitro which encodes the genes necessary to produce a secondary vector in vitro or in vivo. In use, the secondary vector carries one or more selected genes for insertion into the target cell. The selected genes may be one or more marker genes and/or therapeutic genes.

The primary and secondary viral vector may be a variety of different retroviral vectors, such as lentiviral, or in the case of multiple primary viral vectors, they may be a mixture of vectors of different viral origin. In whichever case, the secondary viral vectors are preferably defective in that they are incapable of independent replication. Thus, they are capable of entering a target cell and delivering the secondary vector sequences, but not of replicating so as to go on to infect further target cells.

In the case where the hybrid viral vector system comprises more than one primary vector to encode the secondary vector, all of the primary vectors will be used to infect a primary target cell population, usually simultaneously. The preferred single or multiple primary viral vectors are MLV vectors. The secondary viral vector is preferably a lentiviral vector. In one preferred embodiment the second viral vector is derived from HIV. The construction of a retro-lentiviral system is described in the Examples. The secondary vector is produced by expression of essential genes for assembly and packaging of a defective viral vector particle, within the host cell. It is defective in that it is incapable of independent replication. Thus, once the secondary retroviral vector has transduced a target cell, it is incapable of spreading by replication to any further target cells.

The secondary vector may be produced from expression of essential genes for retroviral vector production encoded in the DNA of the primary vector. Such genes may include a gag-pol gene from a retrovirus, an envelope gene from an enveloped virus, or any other protein, sugar, lipid or complex of these, capable of mediating cell entry and a defective retroviral genome containing one or more therapeutic genes. The retroviral genome contains in general terms sequences to enable reverse transcription, at least part of a 5' long terminal repeat (LTR), at least part of a 3' LTR and a packaging signal.

In a particularly preferred embodiment we have developed a stable, constitutive HIV-1 packaging system, herein referred to as "STAR". This system rapidly and reproducibly generates large batches of high titre vectors, which allows extensive safety control tests, an important aspect for the clinical use. In this system, high level expression of HIV-1 Gag-pol was achieved by transducing cells, preferably 293 T cells, with a murine leukaemia virus (MLV) vector coding for codon-optimised gag-pol gene (Kotsopoulo, E., et al. *J. Virol.* 74, 4839-4852 (2000)). Subsequently, the HIV-1 regulatory proteins, Tat and Rev, for efficient vector genome production and gammaretrovirus envelopes (Env) were introduced, resulting in packaging cell lines producing empty vector particles. Upon introduction of HIV vector genomes encoding an NOI, high-titre HIV-NOI vectors were produced.

In a preferred embodiment, the secondary vector is also safe for in vivo use in that incorporated into it are one or more safety features which eliminate the possibility of recombination to produce an infectious virus capable of independent replication.

To ensure that it is replication defective the secondary vector may be encoded by a plurality of transcription units, which may be located in a single or in two or more primary vectors. Thus, there may be a transcription unit encoding the secondary vector genome, a transcription unit encoding gag-pol and a transcription unit encoding env. Alternatively, two or more of these may be combined. For example, nucleic acid sequences encoding gag-pol and env, or env and the genome, may be combined in a single transcription unit. Ways of achieving this are known in the art.

Transcription units as described herein are regions of nucleic acid containing coding sequences and the signals for achieving expression of those coding sequences independently of any other coding sequences. Thus, each transcription unit generally comprises at least a promoter, an enhancer and a polyadenylation signal. The promoter and enhancer of the transcription units encoding the secondary vector are preferably strongly active, or capable of being strongly induced, in the target cells under conditions for production of the secondary viral vector. The promoter and/or enhancer may be constitutively efficient, or may be tissue or temporally restricted in their activity.

Safety features which may be incorporated into the hybrid viral vector system are described below. One or more such features may be present.

Firstly, sequence homology between the sequences encoding the components of the secondary vector may be avoided by deletion of regions of homology. Regions of homology allow genetic recombination to occur. In a particular embodiment, three transcription units are used to construct a secondary retroviral vector. A first transcription unit contains a retroviral gag-pol gene under the control of a non-retroviral promoter and enhancer. A second transcription unit contains a retroviral env gene under the control of a non-retroviral promoter and enhancer. A third transcription unit comprises a defective retroviral genome under the control of a non-retroviral promoter and enhancer. In the native retroviral genome, the packaging signal is located such that part of the gag sequence is required for proper functioning. Normally when retroviral vector systems are constructed therefore, the packaging signal, including part of the gag gene, remains in the vector genome. In the present case however, a synthetic gag sequence may be used which lacks homology with the vector.

Secondly, the possibility of replication competent secondary viral vectors may be avoided by pseudotyping the genome of one retrovirus with the envelope protein of another retrovirus or another enveloped virus so that regions of homology between the env and gag-pol components are avoided. In a particular embodiment the retroviral vector is constructed from the following three components. The first transcription unit contains a retroviral gag-pol gene under the control of a non-retroviral promoter and enhancer. The second transcription unit contains the env gene from the alternative enveloped virus, under the control of a non-retroviral promoter and enhancer. The third transcription unit comprises a defective retroviral genome under the control of a non-retroviral promoter and enhancer. It is also envisaged that the primary viral vector may be pseudotyped. Pseudotyping is described below in more detail.

Thirdly, the possibility of replication competent retroviruses can be eliminated by using two transcription units constructed in a particular way. The first transcription unit contains a gag-pol coding region under the control of a promoter-enhancer active in the primary target cell such as a hCMV promoter-enhancer or a tissue restricted promoter-enhancer. The second transcription unit encodes a retroviral genome RNA capable of being packaged into a retroviral particle. The second transcription unit contains retroviral sequences necessary for packaging, integration and reverse transcription and also contains sequences coding for an env protein of an enveloped virus and the coding sequence of one or more therapeutic genes.

The primary retroviral vectors may be replication competent vectors but are more preferably defective retroviral vectors.

Embodiments of the invention described solve one of the major problems associated with production of some viral vectors used in gene therapy, namely that production is transient.

The use of a retroviral vector as the secondary vector is also advantageous because it permits the stable expression of therapeutic genes in the target tissue, including stable expression in proliferating target cells.

Preferably, the secondary viral vector preferentially infects a certain cell type or cell types. More preferably, the secondary vector is a targeted vector, that is it has a tissue tropism which is altered compared to the native virus, so that the vector is targeted to particular cells. The term "targeted vector" is not necessarily linked to the term "target cell". "Target cell" simply refers to a cell which the second vector, whether native or targeted, is capable of infecting or transducing.

For retroviral vectors, targeting may be achieved by modifying the envelope protein. The envelope protein of the retroviral secondary vector needs to be a non-toxic envelope or an envelope which may be produced in non-toxic amounts within the primary target cell, such as for example a MLV amphotropic envelope or a modified amphotropic envelope.

Target cells for the secondary vector according to the invention include but are not limited to haematopoietic cells (including monocytes, macrophages, lymphocytes, granulocytes or progenitor cells of any of these); endothelial cells; tumour cells; stromal cells; astrocytes or glial cells; muscle cells; epithelial cells; and adult or foetal stem cells.

When the secondary vector contains an NOI, preferably this second transcription unit is under the control of a promoter-enhancer which is preferentially active in a diseased location within the body such as an ischaemic site or the micro-environment of a solid tumour. In a particularly preferred embodiment of this aspect of the invention, the second transcription unit is constructed such that on insertion of the genome into the target cell, an intron is generated which serves to reduce expression of the viral env gene and permit efficient expression of a therapeutic gene.

The host cell population may be the same as the target cell population. For example delivery of a primary vector of the invention to tumour cells leads to replication and generation of further vector particles which can transduce further tumour cells. Alternatively, the target cell population may be different from the host cell population. In this case the host cells serve as an endogenous factory within the body of the treated individual and produce additional vector particles which can infect the target cell population. For example, the host cell population may be haematopoietic cells transduced by the primary vector in vivo or ex vivo. The target cells are then delivered to or migrate to a site within the body such as a tumour and produce the secondary vector particles, which are capable of transducing for example tumour cells within a solid tumour.

The invention permits the localised production of high titres of defective retroviral vector particles in vivo at or near the site at which action of a therapeutic protein or proteins is required with consequent efficient transduction of target cells. In this case the primary vector will also be replication defective.

The invention also permits the production of retroviral vectors such as MLV-based vectors in non-dividing and slowly-dividing cells in vivo. It had previously been possible to produce MLV-based retroviral vectors only in rapidly dividing cells such as tissue culture-adapted cells proliferating in vitro or rapidly dividing tumour cells in vivo. Extending the range of cell types capable of producing retroviral vectors is advantageous for delivery of genes to the cells of solid tumours, many of which are dividing slowly, and for the use of non-dividing cells such as endothelial cells and cells of various haematopoietic lineages as endogenous factories for the production of therapeutic protein products.

Retroviruses

The concept of using retroviral vectors for gene therapy and gene delivery is well known (Verma and Somia (1997) *Nature* 389:239-242).

There are many retroviruses. For the present application, the term "retrovirus" includes: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including spumaviruses and lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

In a preferred embodiment, the secondary retroviral vector at least is derivable from a lentivirus. Lentiviruses also belong to the retrovirus family, but they can infect both dividing and non-dividing cells (Lewis et al (1992) EMBO J. 3053-3058).

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

As used herein HIV encompasses all designations assigned to those viruses implicated as causative agents of acquired immunodeficiency syndrome (AIDS) and AIDS-related complex (ARC), such as HIV, e.g., HIV-1 and HIV-2, and HTLV, e.g., HTLV-III. Of the two major HIV types, HIV-1 and HIV-2, HIV-1 is the predominant species around the world. To date, two major groups of HIV-1 exist, "M" and "O". The virus that causes the great majority of HIV-1 infections are in the M group. The O group isolates are genetically quite distant from the M group. HIV-1 subtypes of the M group include subtypes A-J.

Details on the genomic structure of some lentiviruses may be found in the art. By way of example, details on HIV and EIAV may be found from the NCBI Genbank database (i.e., Genome Accession Nos. AF033819 and AF033820 respectively). Details of HIV variants may also be found at http address hiv-web.lanl.gov. Details of EIAV variants may be found through http address www.ncbi.nlm.nih.gov.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

For the viral genome, the site of transcription initiation is at the boundary between U3 and R in one LTR and the site of poly (A) addition (termination) is at the boundary between R and U5 in the other LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes which code for proteins other than gag, pol and env. Examples of additional genes include in HIV, one or more of vif vpr, vpx, vpu, tat, rev and nef EIAV has (amongst others) the additional gene S2.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

Vector Systems

Retroviral vector systems, such as lentiviral vector systems have been proposed as a delivery system for inter alia the transfer of a NOI to one or more sites of interest. The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, A. et al., supra).

As used herein the term "vector system" means a vector particle capable of transducing a recipient cell with an NOI.

A vector particle includes the following components: a vector genome, which may contain one or more NOIs, a nucleocapsid encapsidating the nucleic acid, and a membrane surrounding the nucleocapsid.

The term "nucleocapsid" refers to at least the group specific viral core proteins (gag) and the viral polymerase (pol) of a retrovirus genome. These proteins encapsidate the packagable sequences and are themselves further surrounded by a membrane containing an envelope glycoprotein.

Once within the cell, the RNA genome from a retroviral vector particle is reverse transcribed into DNA and integrated into the DNA of the recipient cell.

The term "vector genome" refers to both to the RNA construct present in the retroviral vector particle and the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof which need not necessarily be obtained from a retrovirus such as a lentivirus but instead could be derived therefrom. By way of example, the sequence may be prepared synthetically or by use of recombinant DNA techniques. Preferably the genome comprises a psi region (or an analogous component which is capable of causing encapsidation).

Preferably the primary retroviral vector is a self-inactivating (SIN) vector system.

Preferably the primary retroviral vector contains an internal promoter to drive the expression of the NOI of interest.

Preferably the primary retroviral vector contains a split intron sequence (J Virol 2000 March; 74(5):2365-71. Split-intron retroviral vectors; enhanced expression with improved safety. Ismail S I, Kingsman S M, Kingsman A J, Uden M.).

Preferably the primary retroviral vector contains a split polyA sequence (J Virol 2001 January; 75(1):199-204. Use of intron-disrupted polyadenylation sites to enhance expression and safety of retroviral vectors. Ismail S I, Rohll J B, Kingsman S M, Kingsman A J, Uden M.).

Preferably the secondary retroviral vector is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene.

Preferably a recombinase assisted mechanism is used which facilitates the production of high titre regulated retroviral vectors from the producer cells of the present invention.

As used herein, the term "recombinase assisted system" includes but is not limited to a system using the Cre recombinase/loxp recognition sites of bacteriophage P1 or the site-specific FLP recombinase of S. cerevisiae which catalyses recombination events between 34 bp FLP recognition targets (FRTs).

The site-specific FLP recombinase of S. cerevisiae which catalyses recombination events between 34 bp FLP recognition targets (FRTs) has been configured into DNA constructs in order to generate high level producer cell lines using recombinase-assisted recombination events (Karreman et al. (1996) NAR 24:1616-1624). A similar system has been developed using the Cre recombinase/loxp recognition sites of bacteriophage P1 (see PCT/GB00/03837; Vanin et al. (1997) J. Virol 71:7820-7826). This was configured into a lentiviral genome such that high titre lentiviral producer cell lines were generated.

By using producer/packaging cell lines of the present invention, it is possible to propagate and isolate quantities of viral vector particles (e.g., to prepare suitable titres of the viral vector particles) for subsequent transduction of, for example, a site of interest (such as adult brain tissue). Producer cell lines are usually better for large scale production or vector particles.

Producer cells/packaging cells can be of any suitable cell type. Producer cells are generally mammalian cells but can be, for example, insect cells.

As used herein, the term "producer cell" or "vector producing cell" refers to a cell which contains all the elements necessary for production of retroviral vector particles.

Preferably, the producer cell is obtainable from a derived stable cell line.

As used herein, the term "derived stable producer cell line" is a transduced producer cell line which has been screened and selected for high expression of a marker gene. Such cell lines support high level expression from the viral genome. The term "derived producer cell line" is used interchangeably with the term "derived stable producer cell line" and the term "stable producer cell line".

Preferably the derived producer cell line is an HIV or EIAV producer cell line.

Preferably the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as gag-pol and env, which may be codon optimised) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines may be readily prepared (see also WO 92/05266), and utilised to create producer cell lines for the production of retroviral vector particles. As already mentioned above, a summary of the available packaging lines is presented in "Retroviruses".

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. Preferably the packaging cell line is a human cell line. Examples of suitable cell lines include: HEK293, 293-T, TE671, HT1080 or HeLa, more preferably 293T or HT1080, even more preferably 293T.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells.

It is highly desirable to use high-titre virus preparations in both experimental and practical applications. Techniques for increasing viral titre include using a psi plus packaging signal as discussed above and concentration of viral stocks.

As used herein, the term "high titre" means an effective amount of a viral vector or particle which is capable of transducing a target site.

As used herein, the term "effective amount" means an amount of a regulated retroviral vector particle which is sufficient to induce expression of the NOIs at a target site.

A high-titre viral preparation for a producer/packaging cell is usually of the order of $10^5$ to $10^7$ t.u. per ml. (The titer is expressed in transducing units per ml (t.u./ml) as titred on a standard cell line, such as 293T or D17). For transduction in some tissues, it may be necessary to use very small volumes, so the viral preparation is concentrated by ultracentrifugation, low-speed centrifugation or cross-slow filtration.

The expression products encoded by the NOIs may be proteins which are secreted from the cell. Alternatively the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighbouring or distant (e.g., metastatic), which possess a common phenotype.

The presence of a sequence termed the central polypurine tract (cPPT) may improve the efficiency of gene delivery to non-dividing cells (see WO 00/31200). This cis-acting element is located, for example, in the EIAV polymerase coding region element. Preferably the genome of the vector system used in the present invention comprises a cPPT sequence. In addition, or in the alternative, the viral genome may comprise a post-translational regulatory element and/or a translational enhancer.

The NOIs may be operatively linked to one or more promoter/enhancer elements. Transcription of one or more NOI may be under the control of viral LTRs or alternatively promoter-enhancer elements can be engineered in with the transgene. Preferably the promoter is a strong promoter such as CMV. The promoter may be a regulated promoter. The promoter may be tissue-specific.

Minimal Systems

It has been demonstrated that a primate lentivirus minimal system can be constructed which requires none of the HIV/SIV additional genes vif vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g., HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

Thus, preferably, the retroviral vector used in the invention is devoid of at least tat and S2 (if it is an EIAV vector system), and possibly also vif, vpr, vpx, vpu and nef More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimisation (see below) or by replacement with other functional equivalent systems such as the MPMV system. As expression of the codon optimised gag-pol is REV independent, RRE can be removed from the gag-pol expression cassette, thus removing any potential for recombination with any RRE contained on the vector genome.

In a preferred embodiment the viral genome of the first aspect of the invention lacks the Rev response element (RRE).

In a preferred embodiment, the system used in the present invention is based on a so-called "minimal" system in which some or all of the additional genes have be removed.

Codon Optimisation

Codon optimisation has previously been described in WO99/41397 and WO01/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corrsponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with the exception of the sequence encompassing the frameshift site.

The gag-pol gene comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In a highly preferred embodiment, codon optimisation was based on lightly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found at http address hiv-web.lan-1.gov. Details of EIAV clones may be found at the NCBI database at http address www.ncbi.nlm.nih.gov.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the retroviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titre. To date efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-termnial 360 or so nucleotides in gag leads to an increase in vector titre. Thus, preferably, the retroviral vector genome includes a gag sequence which comprises one or more deletions, more preferably the gag sequence comprises about 360 nucleotides derivable from the N-terminus.

Pseudotyping

In the design of viral vector systems it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

Thus, in accordance with a preferred embodiment, the primary and/or secondary viral vector is pseudotyped.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847.

Pseudotyping can improve retroviral vector stability and transduction efficiency. A pseudotype of murine leukemia virus packaged with lymphocytic choriomeningitis virus (LCMV) has been described (Miletic et al (1999) J. Virol. 73:6114-6116) and shown to be stable during ultracentrifugation and capable of infecting several cell lines from different species. Other envelope proteins, such as envelope proteins from the Ebola virus may also be used.

In one embodiment of the present invention, the vector system may be pseudotyped with LMCV env protein.

In another embodiment of the present invention, the vector system may be pseudotyped with an envelope proteins from the Ebola virus.

In another embodiment of the present invention, the vector system may be pseudotyped with an envelope proteins from an alphavirus.

In another embodiment use may be made of env derived from gammaretrovirus strains, such as amphotropic MLV (MLV-A), gibbon ape leukaemia virus (GALV) and the feline endogenous virus RD114 (Miller A D et al. *J Virol* 1991; 65: 2220-2224; Cosset, F-L., et al. *J. Virol.* 69, 7430-7436 (1995)). The cellular receptors for these env are different from each other and found on a wide variety of human cell types (Sommerfelt M A, Weiss R A. *Virology* 1990; 176: 58-69). MLV vectors bearing these env have been used for the transduction of several clinically relevant cell types such as lymphocytes and $CD34^+$ progenitor cells both in vitro (Uckert W et al. *Hum Gene Ther* 2000; 11: 1005-1014; Kelly P F et al. *Blood* 2000; 96: 1206-1214; Hanawa H et al. *Mol Ther* 2002; 5: 242-251) and ex vivo (Blaese R M et al. *Science* 1995; 270: 475-480; Bordingnon C et al. *Science* 1995; 270: 470-475; Cavazzana-Calvo M et al. *Science* 2000; 288: 669-672; Abonour R et al. *Nat Med* 2000; 6: 652-658).

The mature gammaretrovirus env consists of a trimer of heterodimers. Each dimer is composed of the extra-viral surface subunit (SU) and the membrane spanning subunit (TM). In the mature protein SU and TM are connected via several non-covalent interactions (Gliniak B C, et al. *J Biol Chem* 1991; 266: 22991-22997) and a labile disulphide bond (Pinter A et al. *J Virol* 1997; 71: 8073-8077).

High titre vectors, such as HIV-1 vectors, produced from cells according to the present invention and pseudotyped with gammaretroviral env may be advantageous in many clinical and experimental settings compared to other systems, including transiently produced HIV-1 (VSV-G).

The present invention may also make use of a mutant, variant, homologue or fragment of a gammaretroviral Env. For example, the cytoplasmic tail of RD114 may be replaced by that of the MLV envelope or the RD114 env may be modified by replacing the R peptide cleavage site sequence with that of a matrix-capsid cleavage site in HIV-1 Gag to create RDpro.

We have found that the titre of gammaretrovirus pseudotypes can be increased with the use of polybrene and/or spinoculation. The usage of polybrene and spinoculation enhances vector transduction additively.

In another embodiment of the present invention the viral vector system may be pseudotyped with at least a part of a rabies G protein or a mutant, variant, homologue or fragment thereof, or at least a part of a VSV G protein or a mutant, variant, homologue or fragment thereof, or at least a part of a cocal virus glycoprotein (GenBank AF045556) or a mutant, variant, homologue or fragment thereof, or at least a part of a chandipura virus glycoprotein (GenBank J04350) or a mutant, variant, homologue or fragment thereof.

Thus, in one embodiment of the present invention, there is provided the use of a viral vector comprising a heterologous env region, wherein the heterologous env region comprises at least a part of a rabies G protein or a mutant, variant, homologue or fragment thereof, or at least a part of a VSV G protein or a mutant, variant, homologue or fragment thereof, at least a part of a cocal glycoprotein or a mutant, variant, homologue or fragment thereof, or at least a part of a chandipura glycoprotein or a mutant, variant, homologue or fragment thereof to transduce a target adipose tissue site.

The heterologous env region may be encoded by a gene which is present on a producer plasmid. The producer plasmid may be present as part of a kit for the production of viral vector particles suitable for use in the first aspect of the invention.

Rabies G Protein

In another embodiment of the present invention, the vector may be pseudotyped with at least a part of a rabies G protein or a mutant, variant, homologue or fragment thereof.

Teachings on the rabies G protein, as well as mutants thereof, may be found in in WO 99/61639 as well as Rose et al., 1982 J. Virol. 43: 361-364, Hanham et al., 1993 J. Virol., 67, 530-542, Tuffereau et al., 1998 J. Virol., 72, 1085-1091, Kucera et al., 1985 J. Virol 55, 158-162, Dietzschold et al., 1983 PNAS 80, 70-74, Seif et al., 1985 J. Virol., 53, 926-934, Coulon et al., 1998 J. Virol., 72, 273-278, Tuffereau et al., 1998 J. Virol., 72, 1085-10910, Burger et al., 1991 J. Gen. Virol. 72. 359-367, Gaudin et al 1995 J Virol 69, 5528-5534, Benmansour et al 1991 J Virol 65, 4198-4203, Luo et al 1998 Microbiol Immunol 42, 187-193, Coll 1997 Arch Virol 142, 2089-2097, Luo et al 1997 Virus Res 51, 35-41, Luo et al 1998 Microbiol Immunol 42, 187-193, Coll 1995 Arch Virol 140, 827-851, Tuchiya et al 1992 Virus Res 25, 1-13,. Morimoto et al 1992 Virology 189, 203-216, Gaudin et al 1992 Virology 187, 627-632, Whitt et al 1991 Virology 185, 681-688, Dietzschold et al 1978 J Gen Virol 40, 131 -139, Dietzschold et al 1978 Dev Biol Stand 40, 45-55, Dietzschold et al 1977 J Virol 23, 286-293, and Otvos et al 1994 Biochim Biophys Acta 1224, 68-76. A rabies G protein is also described in EP-A-0445625.

The use of rabies G protein provides vectors which, in vivo, preferentially transduce targeted cells which rabies virus preferentially infects. This includes adipose tissue target cells in vivo. For an adipose tissue targeted vector, rabies G from a pathogenic strain of rabies such as ERA may be particularly effective. On the other hand rabies G protein confers a wider target cell range in vitro including nearly all mammalian and avian cell types tested (Seganti et al., 1990 Arch Virol. 34, 155-163; Fields et al., 1996 Fields Virology, Third Edition, vol. 2, Lippincott-Raven Publishers, Philadelphia, New York).

The tropism of the pseudotyped vector particles may be modified by the use of a mutant rabies G which is modified in the extracellular domain. Rabies G protein has the advantage of being mutatable to restrict target cell range. The uptake of rabies virus by target cells in vivo is thought to be mediated by the acetylcholine receptor (AchR) but there may be other receptors to which it binds in vivo (Hanham et al., 1993 J. Virol., 67, 530-542; Tuffereau et al., 1998 J. Virol., 72, 1085-1091). It is thought that multiple receptors are used in the nervous system for viral entry, including NCAM (Thoulouze et al (1998) J. Virol 72(9):7181-90) and p75 Neurotrophin receptor (Tuffereau C et al (1998) Embo J 17(24) 7250-9).

The effects of mutations in antigenic site III of the rabies G protein on virus tropism have been investigated, this region is not thought to be involved in the binding of the virus to the acetylcholine receptor (Kucera et al., 1985 J. Virol 55, 158-162; Dietzschold et al., 1983 Proc Natl Acad Sci 80, 70-74; Seif et al., 1985 J. Virol., 53, 926-934; Coulon et al., 1998 J. Virol., 72, 273-278; Tuffereau et al., 1998 J. Virol., 72, 1085-10910). For example a mutation of the arginine at amino acid 333 in the mature protein to glutamine can be used to restrict viral entry to olfactory and peripheral neurons in vivo while reducing propagation to the central nervous system. These viruses were able to penetrate motor neurons and sensory neurons as efficiently as the wild type virus, yet transneuronal transfer did not occur (Coulon et al., 1989, J. Virol. 63, 3550-3554). Viruses in which amino acid 330 has been mutated are further attenuated, being unable to infect either motor neurons or sensory neurons after intra-muscular injection (Coulon et al., 1998 J. Virol., 72, 273-278).

Alternatively or additionally, rabies G proteins from laboratory passaged strains of rabies may be used. These can be screened for alterations in tropism. Such strains include the following:

| Genbank Accession Number | Rabies Strain |
| --- | --- |
| J02293 | ERA |
| U52947 | COSRV |
| U27214 | NY 516 |
| U27215 | NY 771 |
| U27216 | FLA125 |
| U52946 | SHBRV |
| M32751 | HEP-Flury |

By way of example, the ERA strain is a pathogenic strain of rabies and the rabies G protein from this strain can be used for transduction of neuronal cells. The sequence of rabies G from the ERA strains is in the GenBank database (accession number J02293). This protein has a signal peptide of 19 amino acids and the mature protein begins at the lysine residue 20 amino acids from the translation initiation methionine. The HEP-Flury strain contains the mutation from arginine to glutamine at amino acid position 333 in the mature protein which correlates with reduced pathogenicity and which can be used to restrict the tropism of the viral envelope.

WO 99/61639 discloses the nucleic and amino acid sequences for a rabies virus strain ERA (Genbank locus RAVGPLS, accession M38452).

VSV-G Protein

The envelope glycoprotein (G) of Vesicular stomatitis virus (VSV), a rhabdovirus, is another envelope protein that has been shown to be capable of pseudotyping certain retroviruses.

Its ability to pseudotype MoMLV-based retroviral vectors in the absence of any retroviral envelope proteins was first shown by Emi et al (1991 Journal of Virology 65:1202-1207). WO94/294440 teaches that retroviral vectors may be successfully pseudotyped with VSV-G. These pseudotyped VSV-G vectors may be used to transduce a wide range of mammalian cells. Even more recently, Abe et al (J Virol 1998 72(8) 6356-6361) teach that non-infectious retroviral particles can be made infectious by the addition of VSV-G.

Burns et al (1993 Proc. Natl. Acad. Sci. USA 90: 8033-7) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al 1993 ibid). They have also been shown to be more efficient than traditional amphotropic envelopes for a variety of cell lines (Yee et al, 1994 Proc. Natl. Acad. Sci. USA 91: 9564-9568, Lin, Emi et al, 1991 Journal of Virology 65:1202-1207). VSV-G protein can be used to pseudotype certain retroviruses because its cytoplasmic tail is capable of interacting with the retroviral cores.

The provision of a non-retroviral pseudotyping envelope such as VSV-G protein gives the advantage that vector particles can be concentrated to a high titre without loss of infectivity (Akkina et al, 1996 J. Virol. 70: 2581-5). Retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

WO 00/52188 describes the generation of pseudotyped retroviral vectors, from stable producer cell lines, having vesicular stomatitis virus-G protein (VSV-G) as the membrane-associated viral envelope protein, and provides a gene sequence for the VSV-G protein.

A potential advantage of using the rabies glycoprotein in comparison to the VSV glycoprotein is the detailed knowledge of its toxicity to man and other animals due to the extensive use of rabies vaccines. In particular phase I clinical trials have been reported on the use of rabies glycoprotein expressed from a canarypox recombinant virus as a human vaccine (Fries et al., 1996 Vaccine 14, 428-434), these studies concluded that the vaccine was safe for use in humans.

Mutants, Variants, Homologues and Fragments

In one embodiment of the present invention, the retroviral vector system used in the present invention may be pseudotyped with a mutant, variant, homologue or fragment of an envelope protein.

The term "wild type" is used to mean a polypeptide having a primary amino acid sequence which is identical with the native protein (i.e., the viral protein).

The term "mutant" is used to mean a polypeptide having a primary amino acid sequence which differs from the wild type sequence by one or more amino acid additions, substitutions or deletions. A mutant may arise naturally, or may be created artificially (for example by site-directed mutagenesis). Preferably the mutant has at least 90% sequence identity with the wild type sequence. Preferably the mutant has 20 mutations or less over the whole wild-type sequence. More preferably the mutant has 10 mutations or less, most preferably 5 mutations or less over the whole wild-type sequence.

The term "variant" is used to mean a naturally occurring polypeptide which differs from a wild-type sequence. A variant may be found within the same viral strain (i.e., if there is more than one isoform of the protein) or may be found within a different strains. Preferably the variant has at least 90% sequence identity with the wild type sequence. Preferably the variant has 20 mutations or less over the whole wild-type sequence. More preferably the variant has 10 mutations or less, most preferably 5 mutations or less over the whole wild-type sequence.

Here, the term "homologue" means an entity having a certain homology with the wild type amino acid sequence and the wild type nucleotide sequence. Here, the term "homology" can be equated with "identity".

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e., amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to the subject sequence. Typically, the homologues will comprise the same sequences that code for the active sites etc. as the subject sequence. Although homology can also be considered in terms of similarity (i.e., amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al, 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS *Microbiol Lett* 1999 174(2): 247-50; FEMS *Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with unchanged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e., like-for-like substitution such as basic for basic, acidic for acidic, polar for polar etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allylglycine*, β-alanine*, L-α-amino butyric acid*, L-γ-amino butyric acid*, L-α-amino isobutyric acid*, L-e-amino caproic acid* , 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr(methyl)*, L-Phe (4-isopropyl)*, L-Tic(1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The term "fragment" indicates that the polypeptide comprises a fraction of the wild-type amino acid sequence. It may comprise one or more large contiguous sections of sequence or a plurality of small sections. The polypeptide may also comprise other elements of sequence, for example, it may be a fusion protein with another protein. Preferably the polypeptide comprises at least 50%, more preferably at least 65%, most preferably at least 80% of the wild-type sequence.

With respect to function, the mutant, variant, homologue or fragment should be capable of transducing a cell when used to pseudotype an appropriate vector.

The retroviral vector used in the present invention may comprise nucleotide sequences that can hybridise to the nucleotide sequence presented herein (including complementary sequences of those presented herein). In a preferred aspect, the present invention covers nucleotide sequences that can hybridise to the nucleotide sequence of the present invention under stringent conditions (e.g., 65° C. and 0.1 SSC) to the nucleotide sequence presented herein (including complementary sequences of those presented herein).

NOIs

In the present invention one or more NOIs (nucleotide sequences of interest) may be delivered to a target cell in vivo or in vitro.

In accordance with the present invention, it is possible to manipulate the viral genome so that viral genes are replaced or supplemented with one or more NOIs which may be heterologous NOIs.

The term "heterologous" refers to a nucleic acid or protein sequence linked to a nucleic acid or protein sequence to which it is not naturally linked.

In the present invention, the term NOI includes any suitable nucleotide sequence, which need not necessarily be a complete naturally occurring DNA or RNA sequence. Thus, the NOI can be, for example, a synthetic RNA/DNA sequence, a recombinant RNA/DNA sequence (i.e., prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

A retroviral vector genome may generally comprise LTRs at the 5' and 3' ends, suitable insertion sites for inserting one or more NOI(s), and/or a packaging signal to enable the genome to be packaged into a vector particle in a producer cell. There may even be suitable primer binding sites and integration sites to allow reverse transcription of the vector RNA to DNA, and integration of the proviral DNA into the target cell genome. In a preferred embodiment, the lentiviral vector particle has a reverse transcription system (compatible reverse transcription and primer binding sites) and an integration system (compatible integrase and integration sites).

The NOI may encode a protein of interest ("POI"). In this way, a retroviral delivery system could be used to examine the effect of expression of a foreign gene a target cell. For example, a retroviral delivery system could be used to screen a cDNA library for a particular effect on a target site.

The NOI may be capable of blocking or inhibiting the expression of a gene in the target site. For example, the NOI may be an antisense sequence or interfering RNA sequence. The inhibition of gene expression using antisense technology is well known.

The NOI or a sequence derived therefrom may be capable of "knocking out" the expression of a particular gene in a target site. There are several "knock out" strategies known in the art. For example, tile NOI may be capable of integrating in the genome of the cells of the target site so as to disrupt expression of the particular gene. The NOI may disrupt expression by, for example, introducing a premature stop codon, by rendering the downstream coding sequence out of frame, or by affecting the capacity of the encoded protein to fold (thereby affecting its function).

Alternatively, the NOI may be capable of enhancing or inducing ectopic expression of a gene in the target site. The NOI or a sequence derived therefrom may be capable of "knocking in" the expression of a particular gene.

Transduced cells which express a particular gene, or which lack the expression of a particular gene have applications in drug discovery and target validation. The expression system could be used to determine which genes have a desirable effect on target tissue cells.

An NOI delivered by the viral delivery system of the present invention may be a selection gene, or a marker gene. Many different selectable markers have been used successfully in retroviral vectors.

An NOI delivered by a retroviral vector of the present invention may be a therapeutic gene—in the sense that the gene itself may be capable of eliciting a therapeutic effect or it may code for a product that is capable of eliciting a therapeutic effect.

In accordance with the present invention, suitable NOIs include those that are of therapeutic and/or diagnostic application such as, but not limited to: sequences encoding cytokines, chemokines, hormones, antibodies, anti-oxidant molecules, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group). The NOIs may also encode pro-drug activating enzymes.

As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies.

The term "mimetic" relates to any chemical which may be a peptide, polypeptide, antibody or other organic chemical which has the same binding specificity as the antibody.

The term "derivative" as used herein includes chemical modification of an antibody. Illustrative of such modifications would be replacement of hydrogen by an alkyl, acyl, or amino group.

Screening Methods

In further aspect the present invention also relates to a screening method and modulating factors isolatable by such methods, and uses for such factors.

In one embodiment, the present invention provides method for screening for modulating factors for cells, which comprises the following steps:
(i) providing a target cell;
(ii) transducing the cell with a cDNA library capable of encoding a plurality of candidate compounds using a retroviral vector of the present invention;
(iii) screening for a candidate compound capable of modulating an activity of the target cell.

The cDNA library may be a ribozyme library constructed in a lentiviral vector. The ribozyme library can include but is not limited to a hammerhead ribozyme, an EGS or a group II intron ribozyme. The ribozyme library may be used to transduce cell types of interest in vitro and in vivo. These cells can then be screened for the phenotype of interest. The gene or genes affected by the ribozyme can be elucidated by PCR analysis of the ribozyme. For general teachings on ribozymes, see WO 99/41397.

Preferably the retroviral vector is a lentiviral vector. The advantage of doing this with a lentiviral vector is that it allows the transduction of primary (non-dividing) cells.

Pharmaceutical Compositions

The present invention also provides the use of a retroviral vector of the invention in the manufacture of a pharmaceutical composition. The pharmaceutical composition may be used to deliver a NOI to a target cell in need of same.

The pharmaceutical composition may be used for treating an individual by gene therapy, wherein the composition comprises or is capable of producing a therapeutically effective amount of a retroviral vector system according to the present invention.

The method and pharmaceutical composition of the invention may be used to treat a human or animal subject. Preferably the subject is a mammalian subject. More preferably the subject is a human. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the viral entry into the target tissue site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The vector system used in the present invention may conveniently be administered by direct injection into the patient.

Diseases

The delivery of one or more therapeutic genes by a vector system according to the present invention may be used alone or in combination with other treatments or components of the treatment.

For example, the retroviral vector of the present invention may be used to deliver one or more NOI(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the retroviral vector of the present invention may be used to deliver one or more NOI(s) useful in the treatment of disorders listed in WO-A-

98/07859. For ease of reference, part of that list is now provided: cytokine and cell proliferation/differentiation activity; immunosuppressant or immunostimulant activity (e.g., for treating immune deficiency, including infection with human immune deficiency virus; regulation of lymphocyte growth; treating cancer and many autoimmune diseases, and to prevent transplant rejection or induce tumour immunity); regulation of haematopoiesis, e.g., treatment of myeloid or lymphoid diseases; promoting growth of bone, cartilage, tendon, ligament and nerve tissue, e.g., for healing wounds, treatment of burns, ulcers and periodontal disease and neurodegeneration; inhibition or activation of follicle-stimulating hormone (modulation of fertility); chemotactic/chemokinetic activity (e.g., for mobilising specific cell types to sites of injury or infection); haemostatic and thrombolytic activity (e.g., for treating haemophilia and stroke); antiinflammatory activity (for treating e.g., septic shock or Crohn's disease); as antimicrobials; modulators of e.g., metabolism or behaviour; as analgesics; treating specific deficiency disorders; in treatment of e.g., psoriasis, in human or veterinary medicine.

In addition, or in the alternative, the retroviral vector of the present invention may be used to deliver one or more NOI(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e., inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g., retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g., following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplanTation or other transplantation complications and/or side effects, inflammatory and/or immune complications and side effects of gene therapy, e.g., due to infection with a viral carrier, or inflammation associated with AIDS, to suppress or inhibit a humoral and/or cellular immune response, to treat or ameliorate monocyte or leukocyte proliferative diseases, e.g., leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The present invention also provides a pharmaceutical composition for treating an individual by gene therapy, wherein the composition comprises a therapeutically effective amount of the retroviral vector of the present invention comprising one or more deliverable therapeutic and/or diagnostic NOI(s) or a viral particle produced by or obtained from same. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The delivery of one or more therapeutic genes by a vector system according to the invention may be used alone or in combination with other treatments or components of the treatment. Diseases which may be treated include, but are not limited to: cancer, neurological diseases, inherited diseases, heart disease, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, fusion proteins, hormones, membrane proteins, vasoactive proteins or peptides, cytokines, chemokines, antiviral proteins, antisense RNA and ribozymes.

In a preferred embodiment of a method of treatment according to the invention, a gene encoding a pro-drug activating enzyme is delivered to a tumour using the vector system of the invention and the individual is subsequently treated with an appropriate pro-drug. Examples of pro-drugs include etoposide phosphate (used with alkaline phosphatase Senter et al., 1988 Proc. Natl. Acad. Sci. 85: 4842-4846); 5-fluorocytosine (with Cytosine deaminase Mullen et al., 1994 Cancer Res. 54: 1503-1506); Doxorubicin-N-p-hydroxyphenoxyacetamide (with Penicillin-V-Amidase (Kerr et al., 1990 Cancer Immunol. Immunother. 31: 202-206); Para-N-bis(2-chloroethyl) aminobenzoyl glutamate (with Carboxypeptidase G2); Cephalosporin nitrogen mustard carbamates (with b-lactamase); SR4233 (with P450 Reducase); Ganciclovir (with HSV thymidine kinase, Borrelli et al., 1988 Proc. Natl. Acad. Sci. 85: 7572-7576) mustard pro-drugs with nitroreductase (Friedlos et al., 1997 J Med Chem 40: 1270-1275) and Cyclophosphamide or Ifosfamide (with a cytochrome P450 Chen et al., 1996 Cancer Res 56: 1331-1340).

EXAMPLES

The following examples are intended to illustrate but not limit the invention.

Infection of cells with human immunodeficient virus type 1 (HIV-1) can result in cultures that stably produce infectious virus (Hoxie, J. A., et al. *Science* 229, 1400-1402 (1985)). However, attempts to make stable HIV-1 based vector packaging cells by transfection of plasmids encoding HIV-1 gag-pol have resulted in cells which secrete only low levels of p24 antigen (20-80 ng/ml) (Ott, D. E., et al. *J. Virol.* 69, 2443-2450 (1995); Srinivasakumar, N., et al. *J. Virol.* 71, 5841-5848 (1997); Corbeau, P., et al. *Proc. Natl. Acad. Sci. USA* 93, 14070-14075 (1996)) compared to the 1000 ng/ml secreted by some HIV-1 infected cells lines (Carroll, R., et al. *J. Virol.* 68, 6047-6051 (1994)). It has been speculated that this might be due to the cytotoxicity of HIV-1 protease (Kaplan, A. H. & Swanstrom R. *Proc Natl Acad Sci USA* 88, 4528-4532 (1991)) and has led to the construction of packaging cell lines in which HIV-1 Gag-pol expression can be induced (Sparacio, S., et al. *Mol Ther.* 3, 602-612 (2001); Kaul, M., et al. *Virology* 249, 167-174 (2001); Klages, N., et al. *Mol Ther.* 2, 170-176 (2000); Farson, D. et al. *Hum Gene Ther.* 12, 981-997 (2001).

We have demonstrated that introduction of HIV-1 Gag-pol expression cassettes using a retroviral vector based on murine leukaemia virus (MLV) allowed stable, long-term, high level (up to 850 ng/ml) expression of HIV-1 Gag. HT1080 or 293T-based packaging cells were constructed expressing codon optimised HIV-1 Gag-pol (11), HIV-1 Tat and Rev and envelope proteins of C-type retroviruses. Introduction of an HIV-1 vector resulted in producer cells that could make up to $10^7$ 293T infectious units/ml (20 293T infectious units/cell/day) for 3 months in culture.

Experimental Protocol (for Examples 1-4)

Cell lines. HeLa (ATCC CCL-2), 293T, HT1080 (ATCC, CCI-121) and all the derivative clones were grown in Dulbecco's modified Eagle's medium supplemented with 10% fetal calf serum (FCS) and antibiotics.

Plasmids. The HIV-1 packaging (pCMVR8.91) and VSV-G (pMDG) plasmids are described in (Zufferey, R., et al. *Nat Biotechnol.* 15, 871-875 (1997)). pCNC-MCS was constructed by replacing the SacII-NotI short fragment of pCNCG (Soneoka, Y et al. *Nucleic Acids Res.* 23, 628-633 (1995)) with a SacII-XhoI-NotI linker. The SacII-XhoI fragment of pCMVR8.9, which contains HIV-1 gag, pol, rev, tat genes and RRE, was introduced into the SacII-XhoI site of pCNC-MCS to make pCNC-GPRT. pCNC-SYNGP was constructed by introducing the SacII-NotI fragment of pSYNGP (Kotsopoulo, E., et al. *J. Virol.* 74, 4839-4852 (2000)), containing a codon-optimised gag-pol sequence, into the SacII-NotI site of pCNC-MCS. To construct pCNC-GP, an HIV RRE sequence was amplified by PCR using pCMVR8.91 as a template and introduced into the XhoI-NotI site of pCNC-MCS, followed by the introduction of the SacII-SalI fragment of pCMV8.91 into its SacII-XhoI site. pCNC-TAT and pCNC-REV were constructed by introducing Tat and Rev cDNA from pCMVR8.91 into the SacII-XhoI site of pCNC-MCS. pHRSIN-CSGW is described in (Demaison, C. et al. *Hum Gene Ther.* 13, 803-813 (2002)). Its non-self-inactivating derivative pHV was constructed by introducing the NruI-XhoI fragment of pHRSIN-CSGW into the NruI-SalI site of pH7G (Kotsopoulo, E., et al. *J. Virol.* 74, 4839-4852 (2000)). Retroviral envelope vectors pALF and pG+F were reported (Cosset, F-L., et al. *J. Virol.* 69, 7430-7436 (1995); Marandin, A. et al. *Hum Gene Ther.* 9, 1497-1511 (1998)). pRDproLF was constructed by replacing the BclI-ApaI fragment of pRDLF (Cosset, F-L., et al. *J. Virol.* 69, 7430-7436 (1995)) with the BclI-ApaI fragment phCMVRDpro.

Transfection and selection. Transfection was performed using Lipofectamine (Invitrogen). The pCNC-GPRT and pCNC-SYNGP transfected cells were selected with G418 (1 mg/ml) and G418-resistant clones were isolated 2 to 3 weeks later. Cells transfected with the envelope plasmids were selected with phleomycin: 30 µg/ml for pALF, and pRDproLF-transfected cells and 7 µg/ml for pG+F-transfected cells. Phleomycin-resistant colonies were isolated after 3 weeks. For stable transfection of the vector genome plasmids (pHV and pSIN-CSGW), the vector plasmids were co-transfected with pPUR (Clontech) at a ratio of 20:1. After the selection with 3 µg/ml of puromycin for 3 weeks, 15 puromycin-stable colonies were isolated and the other resistant colonies (>500) were harvested as bulk populations.

Vector production and transduction. The infectious CNC-GPRT, CNC-SYNGP, CNC-GP, CNC-REV and CNC-TAT MLV virions were produced by transient transfection of 293 T cells with a weight ratio of 3:2:1 of vector of packaging of VSV-G plasmids using Lipofectamine (Soneoka, Y et al. *Nucleic Acids Res.* 23, 628-633 (1995)). Cell supernatants were concentrated by ultracentrifugation (10,000×g, 1.5 hr) and used for transduction of HeLa. HT1080, 293 T cells. To establish GPRT or SYNGP clones, cells were infected with the CNC-GPRT vector at multiplicity of infection (MOI) of 4 three times, or with the CNC-SYNGP vector of MOI of 2 once. HeLa or HT1080 cells were selected with 1 mg/ml G418 for 3 weeks, 293 T cells were cloned by limiting dilution, and clones screened for p24 expression. For HeLa-GP+R clones, HeLa cells were transduced with the CNC-GP vector at MOI of 4 twice and then selected in G418 for 2 weeks. The G418-resistant cells were further transduced with the CNC-REV vector at MOI of 20 then cloned by limiting dilution. HeLa-GPRT1 and 293T-GPRT1 cells were transduced with the CNC-REV vector at MOI=20, and further cloned by limiting dilution to select HeLa GPRT1+ R1 (1 clone from 22) and 293T GPRT1+R1 cells (1 clone from 32). To establish HT-STAR and STAR cells, HT-SYNGP1 and 293T-SYNGP1 clones were transduced with the Tat- and Rev-expression MLV vectors at MOI=20 each, and cloned by limiting dilution. HT-STAR clone (1 in 28) and STAR clone (1 in 34) were selected after the screening for Tat- and Rev-expression by transfection of pHRSIN-CSGW and pMDG. The VSV-G pseudotyped H7G and HV vectors were produced by transient transfection of 293 T cells with a weight ratio of 3:2:1 of vector to pCMVR8.91 to pMDG plasmids using Lipofectamine. The vector were harvested, passed through a 0.45-µm filter, and concentrated by ultracentrifugation. The vectors were used to transduce the packaging cell lines to establish HIV vector-producing cell lines.

Vector rescue from Gag-pol-stable clones. To assess the ability of the GPRT, GPRT1+R1 cells to package an HIV-1 vector, vector rescue experiments were performed by transient tranfection of pSIN-CSGW and pMDG with a weight ratio of 3:1. In the case of the GP+R cells and the SYNGP cells, Tat and Rev-expressing plasmids, pCNC-REV and pCNC-TAT were also transfected with a weight ratio of 3:1:1:1 of vector to VSV-G to Tat to Rev plasmids.

Virus titration. To determine the titres, a total of $2 \times 10^5$ 239 T cells per well in 24 well plates were inoculated with serial dilutions of the virus supernatants in the presence of 8 µg/ml polybrene for 6 hours. Numbers of infected cells were determined by measurements of eGFP expression by fluorescence-activated cell sorting (FACS) using a FACScan and CELL QUEST software (Becton Dickinson) at least 48 hours later. Titres for each producer cell line were calculated from the data points where 5-20% of the cell population was eGFP-positive.

P24 Immunostaining. Cells were washed twice in phosphate-buffered saline (PBS), spread on multi-well glass slides and air dried. After fixation with acetone for 20 min, the cells were incubated with anti-p24 mouse monoclonal antibody 38:96K (AIDS Reagent MRC Program. 1:200) for 30 min at 37° C., and rinsed twice with PBS before incubating with the secondary antibody, FITC-conjugated goat anti-mouse immunoglobulin, for 30 min at 37° C. Cells were then washed twice with PBS, and observed by confocal microscopy (MRC 1024 [Bio-Rad] equipped with a krypton-argon laser).

P24 ELISA. $1 \times 10^6$ cells were cultured in a 6 well plate with 2 ml OptiMEM (Gibco) for 24 hr and the serially diluted samples were analyzed for detection of p24 by ELISA using Anti-p24 antibody D7320 (Aalto bioreagents, Dublin), EH12EI-AP (MRC ADP reagents, ADP452) and p24 standard (MRC ADP reagents, ADP620).

Immunoblotting analysis. 10 cells were cultured in a 6 well plate with 2 ml OptiMEM for 2 days. Total protein from $5 \times 10^4$ cells was used as cell lysates. The culture supernatants were used after filtration through a 450 nm pore size syringe filter and ultracentrifugation at 100,000 g for 90 min. The samples were separated on 12.5% denaturing SDS polyacrylamide gel. Expression of p24 CA and precursor protein was detected by anti-p24 mouse monoclonal antibody 38:9K.

Safety assays. For detection of RCR or Gag/Pol functional transfer $10^6$ 293T or VAT-7 cells were infected with $2 \times 10^7$ 293T iu of vectors in 6-well plates overnight. After passage and expansion for the time indicated, a fraction of the cells were seeded in a 10 cm dish, and after 3 days the 12 ml of medium was harvested and centrifuged at 1500 g for 90 min at 4° C. The resulting pellet was resuspended in 220 µl OptiMEM and used to infect $2 \times 10^5$ 293 T cells in the presence of 8 µg/ml polybrene. After 4 days, titres were measured by counting the number of green fluorescent colonies. Detection of the Gag-pol sequence transfer was carried out by nested PCR using gag-specific primers and Ampli Taq Gold (Perkin Elmer). F1/R1 and F2/R2 were used for the wild type sequence and SynF1/SynR1 and SynF2/SynR2 for the synthetic gag.

F1:                                        (SEQ ID NO:1)
TGCATCCAGTGCATGCAGGGCCTAT

R1:                                        (SEQ ID NO:2)
TCTTTGCCACAATTGAAACACTTAAC

SynF1:                                     (SEQ ID NO:3)
GGTGCACGCAGGGCCCATCGCACCGG

SynR1:                                     (SEQ ID NO:4)
GCCACAGTTGAAGCACTTGACGATCT

F2:                                        (SEQ ID NO:5)
AGGGGAAGTGACATAGCAGGAACTAC

R2: GCCTTTCTGTATCATTATGGTAGCT (SEQ ID NO:6)

SynF2: ACGGGGCTCAGACATCGCCGGAACGAC (SEQ ID NO:7)

SynR2: AAAGTTGCCGCGCTGCATCATGATGG (SEQ ID NO:8)

1 µg cellular DNA was used as approximately $10^5$ cell equivalents. ¹/₂₀ of the first PCR reaction was used as template for the second round of the nested PCR. Serial dilutions of plasmids pCMVR8.91 and pSYNGP were used to determine sensitivity.

Example 1

The vectors pCNC-GPRT (as shown in FIG. 1B) and pCNC-SYNGP) as shown in FIG. 1C) were constructed by inserting HIV-1 sequences from pCMVR8.91 (Zufferey, R., et al. Nat Biotechnol. 15, 871-875 (1997)) or pSYNGP (Kotsopoulo, E., et al. J. Virol. 74, 4839-4852 (2000)), respectively, into the MLV vector—pCNC-MCS, which is shown in FIG. 1A.

pCNC-GPRT and pCNC-SYNGP were either (a) tranfected directly into HeLa or HT1080 cells, or (b) first packaged into MLV virions using a transient MLV packaging system (Soneoka, Y et al. Nucleic Acids Res. 23, 628-633 (1995)), which were then used to infect HeLa, HT1080 or 293 T cells.

Transfected or infected HeLa and HT1080 were selected in G418 for the presence of the neo gene. Infected 293 T cells were cloned by limiting dilution as the cells are already G418 resistant. Each clone was then analysed by immunofluorescence for the presence of the HIV-1 p24.

FIG. 2 shows that infection, rather than transfection, of HeLa cells with either virus generated a higher frequency of clones that expressed HIV-1 p24.

Examples of results of the immunoflurescence assay are given in FIG. 3, which show that the level of p24 expression in the two rare positive clones generated by transfection of HeLa cells was relatively low.

In all three cell lines infection with the CNC-SYNGP vector generated a higher frequency of positive clones than the CNC-GPRT vector (FIG. 2).

These data confirm that retroviral infection can result in stable HIV-1 Gag-pol expression.

Example 2

Figure 7A:
FIGS. 7A-7C illustrate HIV-based vector constructs used for the establishment of stable HIV-1 producer cell lines.
Figure 7B:

The ability of cells to package an HIV-1 vector was assessed by transient transfection of the vector pSIN-CSGW (Demaison, C. et al. *Hum Gene Ther.* 13, 803-813 (2002)) (shown in FIG. 7B) and a vesicular stomatitis virus (VSV)-G protein expression plasmid (Zufferey, R., et al. *Nat Biotechnol.* 15, 871-875 (1997)). In the case of GP+R cells and SYNGP cells, the Tat and Rev-expressing plasmids, pCNC-REV and pCNC-TAT, were also co-transfected to allow vector expression. Supernatants from the transiently transfected cells were used to infect 293 T cells and GFP expression was monitored.

The effect of additional Rev expression was also examined in the pCNC-GPRT cells by constructing HeLa GPRT1+R1 and 293T GPRT1+R1 clones using the MLV vector CNC-REV to express additional Rev.

Figure 4:
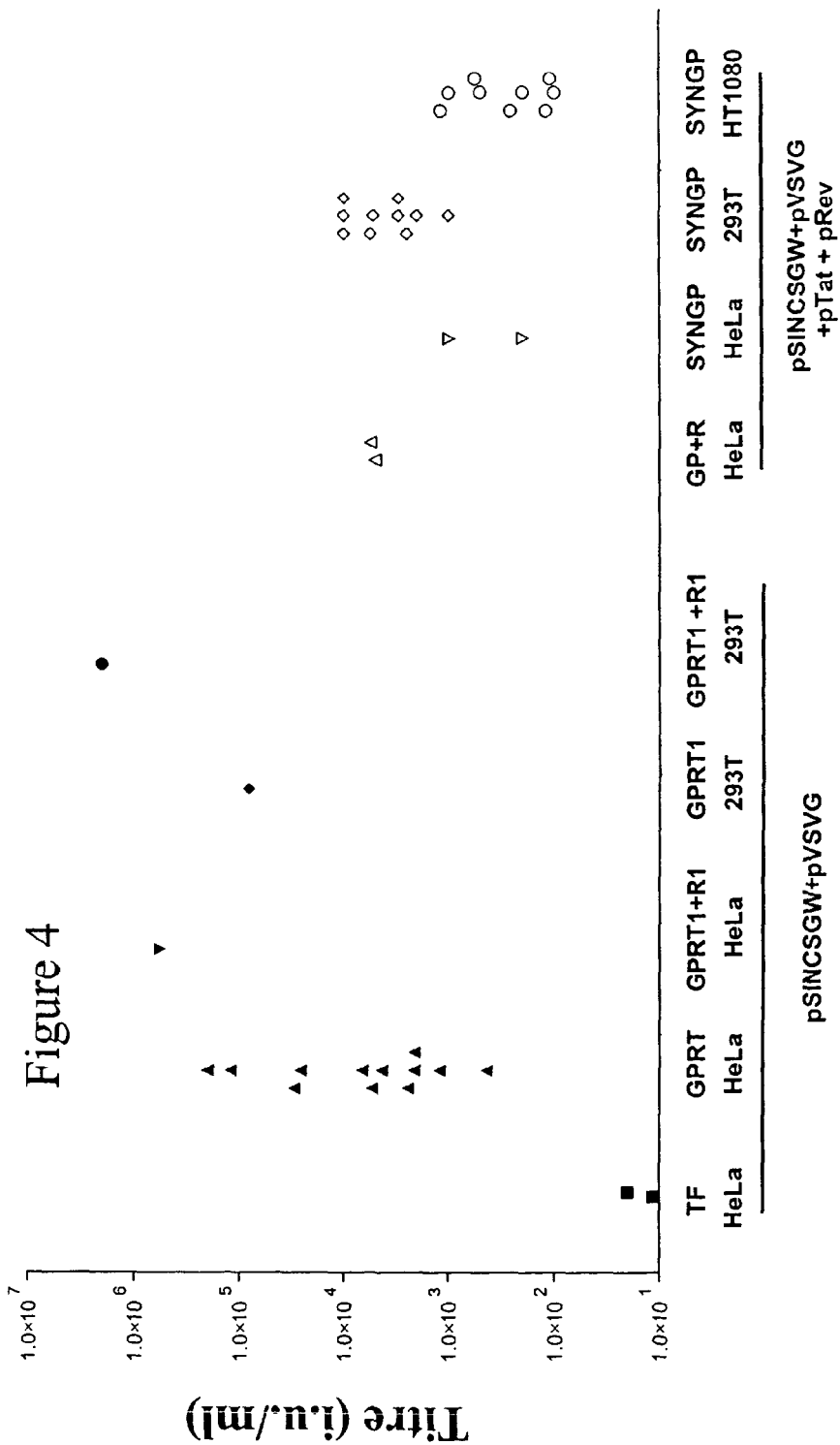
FIG. 4 is a graph illustrating the ability of the cells to package an HIV-1 vector. The ability was assessed by transient transfection of pSIN-CSGW and pMDG with a weight ratio of 3:1. In the case of the GP+R cells and the SYNGP cells, Tat and Rev-expressing plasmids were also transfected with a weight ratio of 3:1:1:1 of vector to VSV-G to Tat to Rev plasmids. Titres were determined on 293 T cells.

FIG. 4 shows that additional Rev enhanced vector production and that the GPRT1+R1 293T clone produced the highest titre in this assay of over $10^6$ i.u./ml. Among the cells expressing SYNGP, the 293T clones gave the highest titre as shown in FIG. 4.

We also examined a so-called "third generation" HIV-1 packaging construct (Dull, T. et al. *J. Virol.* 72, 8463-8471 (1998)) by constructing an MLV vector CNC-GP (shown in FIG. 1D) in which the HIV-1 gag-pol and RRE sequences were from pCMVR8.91 (Zufferey, R., et al. *Nat Biotechnol.* 15, 871-875 (1997)). This was used to infect HeLa cells, with Rev again supplied using the MLV vector CNC-REV, to generate CP+R clones.

FIG. 4 shows that these cells did not give a higher titre than the GPRT1+R1 cells. Clearly, these assays also reflect the relative transfection efficiencies of cells with multiple plasmids.

Figure 5:
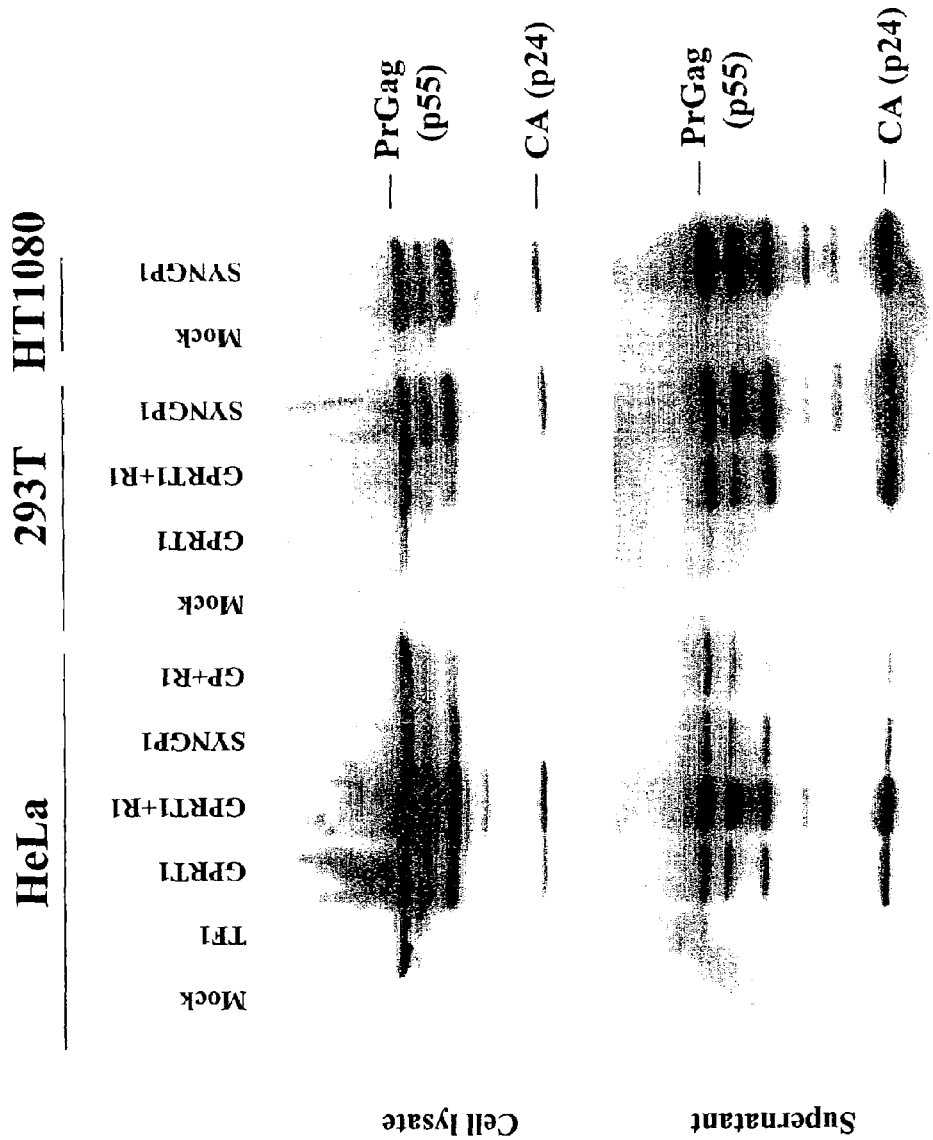
FIG. 5 shows the results of p24 immunoblot of lysates and supernatants from HeLa, 293T and HT1080 clones. Total protein from $5 \times 10^4$ cells was used as cells lysates. 2 ml culture supernatants were ultracentrifuged and the resulting pellet was used as supernatants.
Figure 6:
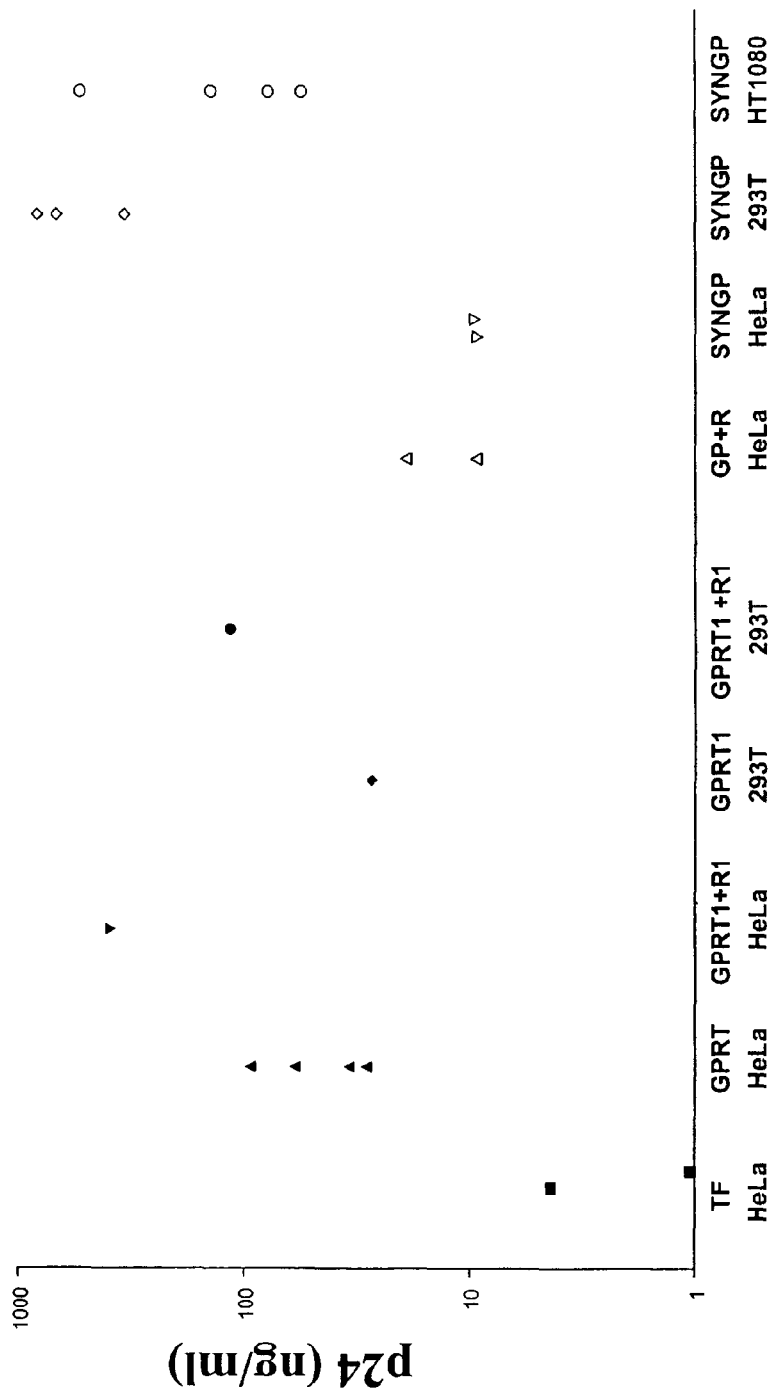
FIG. 6 is a graph showing the level of p24 antigen in the culture supernatants from HIV-1 Gag-stable clones. Detection of p24 antigen in the supernatants of Gag-stable clones was performed on serially diluted samples of culture supernatants by p24 ELISA.

FIG. 5 shows an immuno blot of lysates and supernatants from the HeLa cells transfected with CNC-GPRT and the HeLa cells infected with CNC-GPRT and CNC-SYNGP. Consistent with vector production, increased Rev expression improved the level of HIV-1 Gag expression and secretion by CNC-GPRT. We noted that the ratio of Gag in supernatant to that in lysate was lower in HeLa producer cells and that the ratio of precursor Gag to mature p24 is higher in supernatants from HeLa than HT1080 or 293T. These results suggest that HeLa cells are less efficient in virus release and maturation than other cell lines. FIG. 6 shows p24 levels in cell supernatants; a number of SYNGP 293T and HT1080 clones produce more than HeLa cells.

Example 3

To generate stable packaging cells, we chose to express envelope proteins of MLV and other C-type retroviruses as they are not cytotoxic, can produce relatively high titre pseudotypes of HIV-1 and have been widely used in clinical gene therapy applications. FIG. 5 shows an immuno blot of lysates and supernatants from the HeLa cells transfected with CNC-GPRT and the HeLa cells infected with CNC-GPRT and CNC-SYNGP. Consistent with vector production, increased Rev expression improved the level of HIV-1 Gag expression and secretion by CNC-GPRT. We noted that the ratio of Gag in supernatant to that in lysate was lower in HeLa producer cells and that the ratio of precursor Gag to mature p24 is higher in supernatants from HeLa than HT1080 or 293T. These results suggest that HeLa cells are less efficient in virus release and maturation than other cell lines. FIG. 6 shows p24 levels in cell supernatants; a number of SYNGP 293T and HT1080 clones produce more than HeLa cells.

The 293T GPRT1+R1 cells, a clone of the HT1080 SYNGP1 cells engineered to express Tat and Rev using MLV vectors CNC-TAT and CNC-REV (designated HT-STAR, 1 clone from 28), and a clone of the 293T SYNGP1 cells also engineered to express Tat and Rev using MLV vectors (designated STAR, 1 clone from 34), were chosen for further study.

Figure 7C:

Cells were transfected with the vectors pALF, pRDproLF or pG+F, expressing the envelopes of MLV 4070A (designated Ampho (Cosset, F.-L., et al. *J. Virol.* 69, 7430-7436 (1995))), the feline endogenous virus RD114 with an HIV protease site introduced at the R peptide cleavage site (designated Rdpro), or gibbon ape leukaemia virus (GALV) with an MLV cytoplasmic tail (designated GALV+ (Marandin, A. et al. *Hum Gene Ther.* 9, 1497-1511 (1998))). In each case transfected cells were selected in phleomycin and a clone expressing a high level of envelope was chosen (1 clone from 12). Packaging of three HIV-1 vectors, the Rev independent pH7G (Kotsopoulo, E., et al. *J. Virol.* 74, 4839-4852 (2000)) (FIG. 7A), the Rev-dependent pHRSIN-CSGW (Demaison, C. et al. *Hum Gene Ther.* 13, 803-813 (2002)) (FIG. 7B), or its non-self-inactivating derivative pHV (FIG. 7C) was compared.

FIG. 8 shows that the STAR-Ampho cells produced the highest titre of virus, over $10^7$ i.u./ml from a bulk population after introduction of the vector genome by infection. The presence of Rev in the vector did not affect titre in the STAR cells, suggesting that the level of Rev in the packaging cell was sufficient (FIG. 8).

It was also possible to generate reasonable titre virus following transfection and selection of STAR-Ampho cells, with clones producing up to $10^7$ i.u./ml of self-inactivating vectors (FIG. 8).

The level of viral production by STAR cells was stable after prolonged culture (FIG. 9) and virus could be concentrated by centrifugation to produce stocks with titres up to $5 \times 10^9$ i.u./ml.

Example 3

To generate stable packaging cells, we chose to express envelope proteins of MLV and other C-type retroviruses as they are not cytotoxic, can produce relatively high titre pseudotypes of HIV-1 and have been widely used in clinical gene therapy applications.

The 293T GPRT1+R1 cells, a clone of the HT1080 SYNGP1 cells engineered to express Tat and Rev using MLV vectors CNC-TAT and CNC-REV (designated HT-STAR, 1 clone from 28), and a clone of the 293T SYNGP1 cells also engineered to express Tat and Rev using MLV vectors (designated STAR, 1 clone from 34), were chosen for further study.

Cells were transfected with the vectors pALF, pRDproLF or pG+F, expressing the envelopes of MLV 4070A (designated Ampho (Cosset, F.-L., et al. *J. Virol.* 69, 7430-7436 (1995))), the feline endogenous virus RD114 with an HIV protease site introduced at the R peptide cleavage site (designated Rdpro), or gibbon ape leukaemia virus (GALV) with an MLV cytoplasmic tail (designated GALV+(Marandin, A. et al. *Hum Gene Ther.* 9, 1497-1511 (1998))). In each case transfected cells were selected in phleomycin and a clone expressing a high level of envelope was chosen (1 clone from 12). Packaging of three HIV-1 vectors, the Rev independent pH7G (Kotsopoulo, E., et al. *J. Virol.* 74, 4839-4852 (2000)) (FIG. 7A), the Rev-dependent pHRSIN-CSGW (Demaison, C. et al. *Hum Gene Ther.* 13, 803-813 (2002)) (FIG. 7B), or its non-self-inactivating derivative pHV (FIG. 7C) was compared.

FIG. 8 shows that the STAR-Ampho cells produced the highest titre of virus, over $10^7$ i.u./ml from a bulk population after introduction of the vector genome by infection. The presence of Rev in the vector did not affect titre in the STAR cells, suggesting that the level of Rev in the packaging cell was sufficient (FIG. 8).

It was also possible to generate reasonable titre virus following transfection and selection of STAR-Ampho cells, with clones producing up to $10^7$ i.u./ml of self-inactivating vectors (FIG. 8).

The level of viral production by STAR cells was stable after prolonged culture (FIG. 9) and virus could be concentrated by centrifugation to produce stocks with titres up to $5 \times 10^9$ i.u./ml.

Example 4

To assess the safety of the HIV-1 vectors produced by the stable packaging cells, we first measured replication competent retrovirus (RCR) by infecting 293 T cells with $2 \times 10^7$ iu of the vector pHV produced from clones of either GPRT1+R1-Ampho cells or STARRDpro cells (FIG. 8). After passage of the transduced 293 T cells for 4 weeks, supernatant was concentrated and used to infect fresh 293 T cells. No GFP positive cells were detected by confocal microscopy, indicating that no RCR was present in $2 \times 10^7$ iu of vector.

We also measured transfer of Gag-pol function using a clone of 293 T cells stably expressing pH7G, Ampho envelope and Tat (designated VAT-7 cells). FIG. 10 shows the result of infecting VAT-7 cells with $2 \times 10^7$ iu of transiently or stably produced vectors. Supernatant from the infected VAT-7 cells was taken on the day shown, concentrated and used to infect fresh 293 T cells, which were screened for GFP expression. Vector produced transiently with the wild-type HIV Gag-pol construct pCMVR8.91 showed significant levels of transfer of Gag-pol function. Vector produced stably by its derivative pCNC-GPRT expressed in 293GPRT+R1 cells showed a lower level. In contrast, vector produced transiently by pSYNGP, or stably by its derivative pCNC-SYNGP in STAR cells, showed only sporadic Gag-pol function transfer.

Gag-pol sequence transfer after vector infection of 293 T cells was also detected by nested PCR (FIG. 11); again wild-type Gag-pol showed a higher level of transfer and stable producer cell lines showed a lower level.

Experimental Protocol (for Examples 5 to 10)

Cell lines. All cells were maintained at 37° C., 10% $CO_2$, in Dulbecco's modified Eagle medium (DMEM) (GibCoBRL) supplemented with 10% foetal calf serum (FCS), Penicillin (100 units/ml) and Streptomycin (100 µg/ml), with the exception of NIH 3T3 cells that were maintained in DMEM supplemented with 10% donor calf serum, Penicillin (100 units/ml) and Streptomycin (100 µg/ml). RD+env sequence from pRD+plasmid (Sandrin, V. et al. *Blood* 2002; 100: 823-832) was introduced into RDL plasmid (Cosset, F.-L., et al. *J. Virol.* 69, 7430-7436 (1995)), resulting RD+L plasmid. STAR RD+cells were generated by transfecting RD+L plasmid into STAR cells and used to produce an eGFP encoding HIV-1 vector, HIV-1 (RD+) as previously described. STAR Ampho, STAR RDpro and STAR GALV+ cells producing eGFP encoding HIV-1 vectors, HIV-1 (MLV-A), HIV-1 (RDpro) and HIV-1 (GALV+), respectively were previously described.

Viral vector preparation. Viruses were harvested from 10 cm plates. For virus harvest from STAR cells, $4 \times 10^6$ cells were plated 24 hours before the start of virus harvest. Virus was harvested in 8 ml of either DMEM+10% FCS, plus penicillin and streptomycin or OptiMEM (GibCoBRL) for 48 hours at 37° C. Viral supernatant was then passed through a 0.45-µm-pore-size filter. HIV-1 (VSV-G) virus was generated by transient transfection of 293 T cells with a weight ratio of 3:2:1 of vector (pHV) to packaging (pCMVΔR8.91 (Zufferey, R., et al. *Nat Biotechnol.* 15, 871-875 (1997))) to envelope (pMD-G (Naldini L et al. *Science* 1996; 272: 263-267)) plasmids using Lipofectamine (GibcoBRL) as per the manufacturer's instructions. After washing with OptiMEM, virus was harvested for 48 hours at 37° C. in 8 ml of either DMEM+10% FCS, plus penicillin and streptomycin or OptiMEM. Viral supernatant was then passed through a 0.45-µm-pore-size filter.

Viral titre determination. $2 \times 10^5$ cells were inoculated with serial dilutions of viral supernatant. 48 hours after infection, eGFP titres (iu/ml) were determined by using a fluorescence-activated cell scanner (FACS). Where indicated, titrations were carried out in the presence of 8 µg/ml polybrene (hexadimethrine bromide (Sigma)) or with spinoculation (1,200 g, 2 hours, 25° C.) or both.

Western blotting. Virus in 8 ml of supernatant was pelleted for analysis by ultracentrifugation in an SW41 Beckman Rotor (30,000 rpm, 1 h, 4° C.). Pellets were resuspended in 30 µl of 6× loading buffer diluted in OptiMEM. Samples were boiled for 5 min and frozen at −20° C. until further analysis. Samples were run on 10 or 14% polyacrylamide (SDS) gels. Protein was then transferred onto Hybond ECL nitrocellulose filters (Amersham) using semi-dry transfer apparatus and transfer buffer (39 mM glycine, 48 mM Tris base, 20% methanol).

The TM subunit of MLV-A and GALV envelopes was detected using undiluted supernatant from the rat hybridoma 42/114 (Pinter A et al. *Virology* 1982; 116: 499-516). MLV-A SU was detected with goat polyclonal anti-Rauscher leukemia virus gp70 (Quality Biotech Inc., Camden, N.J.), diluted 1/1000. RD114 SU was detected with goat polyclonal anti-RD114 gp70 (Quality Biotech Inc., Camden, N.J.), diluted 1/5000. HIV-1 CA was detected with a 1:1 mixture of the murine monoclonal antibodies ADP365 and ADP366 (MR-CARD) both diluted 1/200. MLV capsid (CA) was detected with goat polyclonal anti-Rauscher leukemia virus gp70 (Quality Biotech Inc., Camden, N.J.), diluted 1/1000. Blots were developed with horseradish peroxidase-conjugated anti-immunoglobulin (DAKO), diluted 1/1000, and an enhanced chemiluminescence (ECL) kit (Amersham Life Science).

Preparation of human sera. Human peripheral blood was clotted on ice overnight at 4° C. Serum was separated from the clot and aliquoted and frozen at −80° C. (fresh serum preparation) until required or heat inactivated at 56° C. for 45 minutes and then frozen at −80° C. (heat-inactivated serum preparation).

Vector concentration. HIV-1 (VSV-G) and gammaretrovirus pseudotypes were harvested in OptiMEM. 10 ml of each supernatant was concentrated at $10^5$ g using a Beckman L7 ultracentrifuge (SW41 rotor, 35,000 rpm, 1.5 hrs, 4° C.) and the pellet resuspended in 250 μl of OptiMEM. A Beckman L7 ultracentrifuge was also used to concentrate virus at $10^4$ g (SW41 rotor, 15,000 rpm, 3 hrs, 4° C.). Again the pellet was resuspended in 250 μl of OptiMEM. 30 ml of supernatant was concentrated at 3000 g (4,000 rpm, 8 hrs, 4° C.) using a Heraeus Megafuge 2.0R bench top centrifuge (Sepatech). Here the pellet was resuspended in 750 μl of OptiMEM. Virus was concentrated by centrifugal filtration using Centricon Plus-20 (Amicom) filters as per the manufacturers instructions. Here 16 ml of supernatant was added to each filter and the virus recovered in 400 μl.

Gel filtration 100 μl of concentrated viral supernatant was loaded on a Sepharose G PC 3.2/30 column (Amersham) previously equilibrated in OptiMEM. The fractionation was performed using an LKB:μSeperation unit (Amersham) controlled using Smart Manager software. The flow rate of the column was maintained at 40 μl/min and 22 fractions of 100 μl were collected. 25 μl of each fraction of the gel filtration were mixed with 6× loading buffer, boiled and then separated by 10% SDS-PAGE as described above.

Example 5

Generation of STAR Cells Producing Gammaretrovirus Pseudotypes

HIV-1 vectors pseudotyped with the env derived from MLV-A, RD114 and GALV have been produced in transient systems (Hanawa H et al. *Mol Ther* 2002; 5: 242-251; Christodoulopoulos 1, Cannon P M. *J Virol* 2001; 75: 4129-4138; Stitz J et al. *Virology* 2000; 273: 16-20). Previous studies have shown that the titre of lentivirus vectors pseudotyped with the env from GALV and RD114 can be improved with the substitution of their cytoplasmic tail by that of the MLV envelope (Christodoulopoulos 1, Cannon P M. *J Virol* 2001; 75: 4129-4138; Stitz J et al. *Virology* 2000; 273: 16-20; Sandrin, V. et al. *Blood* 2002; 100: 823-832). Therefore, constructs with these substitutions, GALV+ (Marandin, A. et al. *Hum Gene Ther.* 9, 1497-1511 (1998)) and RD+ (Sandrin, V. et al. *Blood* 2002; 100: 823-832) were used. It is possible that these modifications facilitate gammaretrovirus env function by enhancing reaction between HIV-1 protease (PR) and Env (Christodoulopoulos 1, Cannon P M. *J Virol* 2001; 75: 4129-4138; Sandrin, V. et al. *Blood* 2002; 100: 823-832). As an alternative strategy to enhance PR-Env reaction, the RD114 env was also modified by replacing the R peptide cleavage site sequence with that of a matrix-capsid cleavage site in HIV-1 Gag to create RDpro.

The envelope expression plasmids for MLV-A, GALV+, RD+ and RDpro were transfected into STAR cells and clonal cell lines for envelope expression were obtained. These clones were infected with HIV-1 (VSV-G) carrying the vector HV, encoding eGFP. The envelope clones producing highest titre virus were selected. Culture supernatant was harvested and analysed for env incorporation and infectivity on several cell lines.

Figure 12:
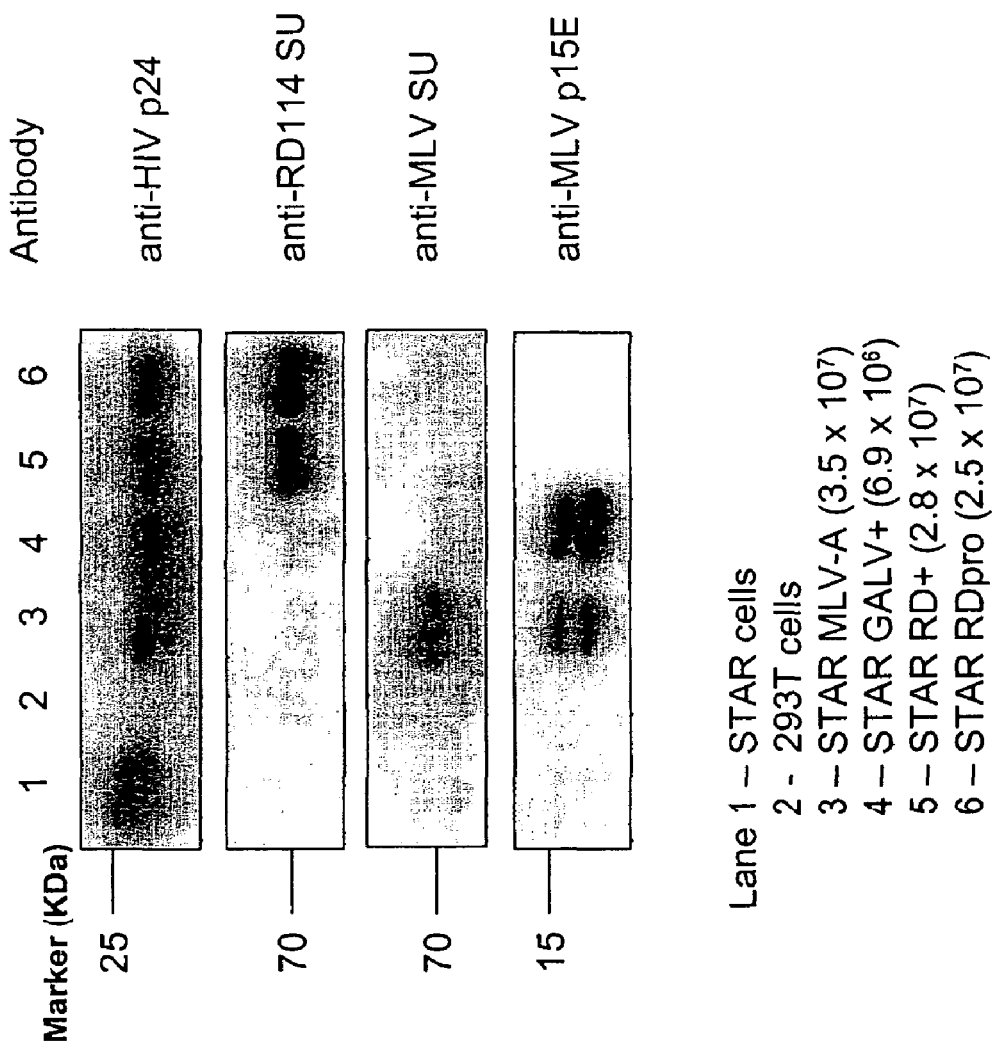
FIG. 12 shows a gel illustrating incorporation of gammaretrovirus envelopes in HIV-1 vectors. Eight milliliter of supernatants were concentrated by ultracentrifugation and the pellet resuspended in 30 µl of loading buffer. 15 µl of each sample was run on 10% (3 upper panels) or 14% (bottom panel) polyacrylamide gels. After transfer membranes were probed with a 1:1 mixture of the murine monoclonal antibodies ADP365 and ADP366 raised against HIV CA (anti-HIV p24), a goat polyclonal serum raised against RD114 SU (anti-RD114 SU), a goat polyclonal serum raised against Rauscher MLV SU (anti-MLV SU) or rat monoclonal antibodies 42/411 raised against MLV TM (anti-MLV p15E). The position of protein markers (in kDa) are shown. Also shown is the eGFP titre of each virus supernatant on 293 T cells in the presence of polybrene.
Figure 13:
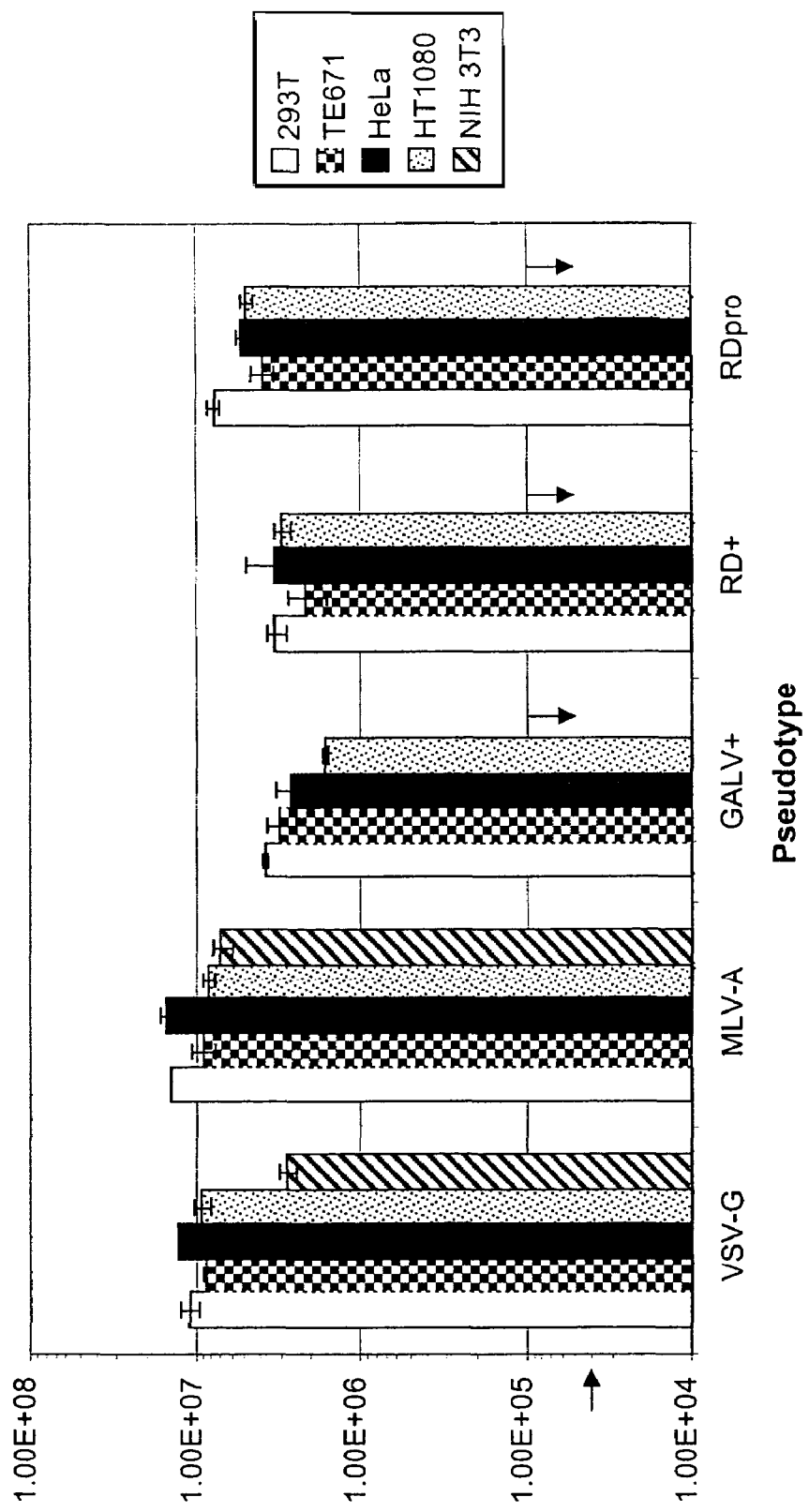
FIG. 13 is a graph showing titration of HIV-1 vectors on a range of cell lines. HIV-1 vectors pseudotyped with gammaretrovirus envelopes (MLV-A, GALV+, RD+ and RDpro) were harvested in OptiMEM from STAR cells or, in the case of HIV-1 (VSV-G) harvested in OptiMEM during transient virus production. Each pseudotype was titrated onto the human cell lines 293T, TE671, HeLa and HT1080 or the murine cell line NIH 3T3 in the presence of polybrene (8 µg/ml). Titre was assayed by FACS 48 hours post infection. Detection limit of $4 \times 10^4$ iu/ml is indicated by arrows.

FIG. 12 shows western blotting of pellets from the ultrafugation of STAR cell supernatants. The presence of vector particles was demonstrated for all STAR cell lines, but not for parental 293 T cells, by the blot probed with anti-HIV-1 p24. Antibodies raised against the RD114 SU recognised the RD114 gp70 in the supernatant from STAR cells expressing RD+ or RDpro envelopes (FIG. 1, lanes 5 and 6), although the two cannot be differentiated. The same membrane was probed with polyclonal antibodies raised against an MLV envelope SU. It has been shown that these antibodies strongly recognise the MLV-A SU but show only weak cross-reaction with the GALV SU (Duisit G, et al. *Hum Gene Ther* 1999; 10: 189-200). Using this serum the MLV-A but not GALV SU could be observed (FIG. 1, lanes 3 and 4). A monoclonal antibody (42/411) that recognises TM from both MLV-A and GALV (Christodoulopoulos 1, Cannon P M. *J Virol* 2001; 75: 4129-4138) did not react with two RD114 constructs as its epitope lies in ectodomain of TM but not in cytoplasmic tail. Both immature (p15) and mature (p12) forms of the MLV-A and GALV+ envelopes could be observed (FIG. 1, lanes 3 and 4). Taken together these results demonstrate correct envelope incorporation.

eGFP titre was measured on several cell lines in comparison with transiently produced HIV-1 (VSV-G) (FIG. 13). All HIV-1 vectors bearing gammaretrovirus env had titres in the range of $10^6$-$10^7$ iu/ml on all human cell lines tested; MLV-A the highest and GALV+ lowest. These titres were similar to or slightly lower than those of HIV-1 (VSV-G). It should be noted that all supernatants of STAR cell lines had p24 at the range of 450-650 ng/ml (data not shown). This compares to about 100 ng/ml for transiently produced HIV-1 (VSV-G), indicating less infectivity per vector particles for gammaretroviral pseudotypes than HIV-1 (VSV-G). As expected vectors with GALV+, RD+ and RDpro did not infect murine NIH3T3 cells, because mice do not have their cognate, functional receptor genes. Correct receptor usage was further demonstrated by receptor interference: HIV-1 (MLV-A) did not infect TE671 cells chronically infected with replication competent MLV-A, HIV-1(GALV+) did not infect TE671 cells chronically infected with GALV and HIV-1 (RD+) and HIV-1 (RDpro) did not infect TE671 chronically infected with RD 114 (data not shown). No cross interference was observed.

Example 6

Stability at 37° C.

Stability of pseudotyped HIV-1 vectors during storage and transduction is an important aspect. We examined HIV-1 vectors bearing gammaretrovirus env as well as HIV-1 (VSV-G) for stability at 37° C., sensitivity to freeze/thaw cycles and inactivation by human sera. In these experiments vectors were harvested in either OptiMEM or DMEM+10% FCS as the absence of FCS in the vector preparation is desirable in many gene therapy applications.

Figure 14:
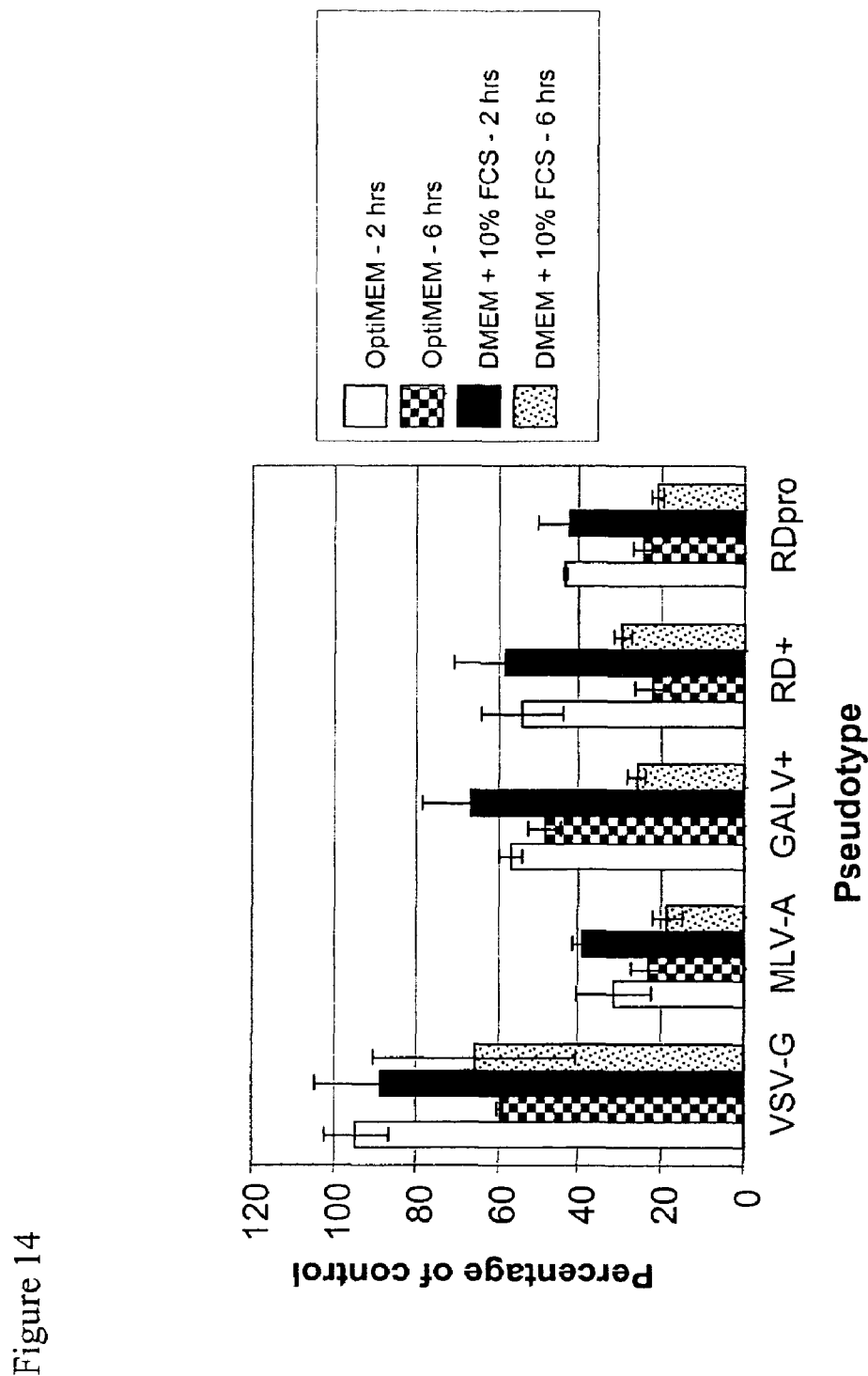
FIG. 14 is a graph showing stability of HIV-1 vectors at 37° C. Vectors were harvested in either OptiMEM or DMEM+10% FCS. Vector stocks were incubated at 37° C. and titrated at different time points. eGFP titre on 293 T cells in the presence of 8 µg/ml polybrene is presented as a percentage of the viral titre before incubation. Values shown are the mean of two experiments and the error bars show the actual data points.

To assess vector stability, decay of infectivity was measured after incubation at 37° C. Aliquots of each virus in OptiMEM or DMEM+10% FCS were incubated at 37° C. and titrated on 293 T cells 2 and 6 hours after the start of incubation (FIG. 14). No substantial difference in stability at 37° C. between virus harvested and incubated in OptiMEM versus that in DMEM+10% FCS was observed. HIV-1 (MLV-A) and HIV-1 (RDpro) appeared to be least stable with a half life less than 2 hours, while HIV-1 bearing either the GALV+ or RD+ appeared to be slightly more stable over 2 hours incubation (half life between 2 and 6 hours). The HIV-1 (VSV-G) virus, meanwhile, had lost only up to 40% of its original titre after 6 hours incubation at 37° C. Virus titration after 24 hours incubation at 37° C. showed that HIV-1 (VSV-G) titre has fallen by 90% (data not shown). The half-life of this virus at 37° C. was therefore shorter than 24 hours.

Example 7

Resistance to Freeze/Thaw Cycling

Figure 15:
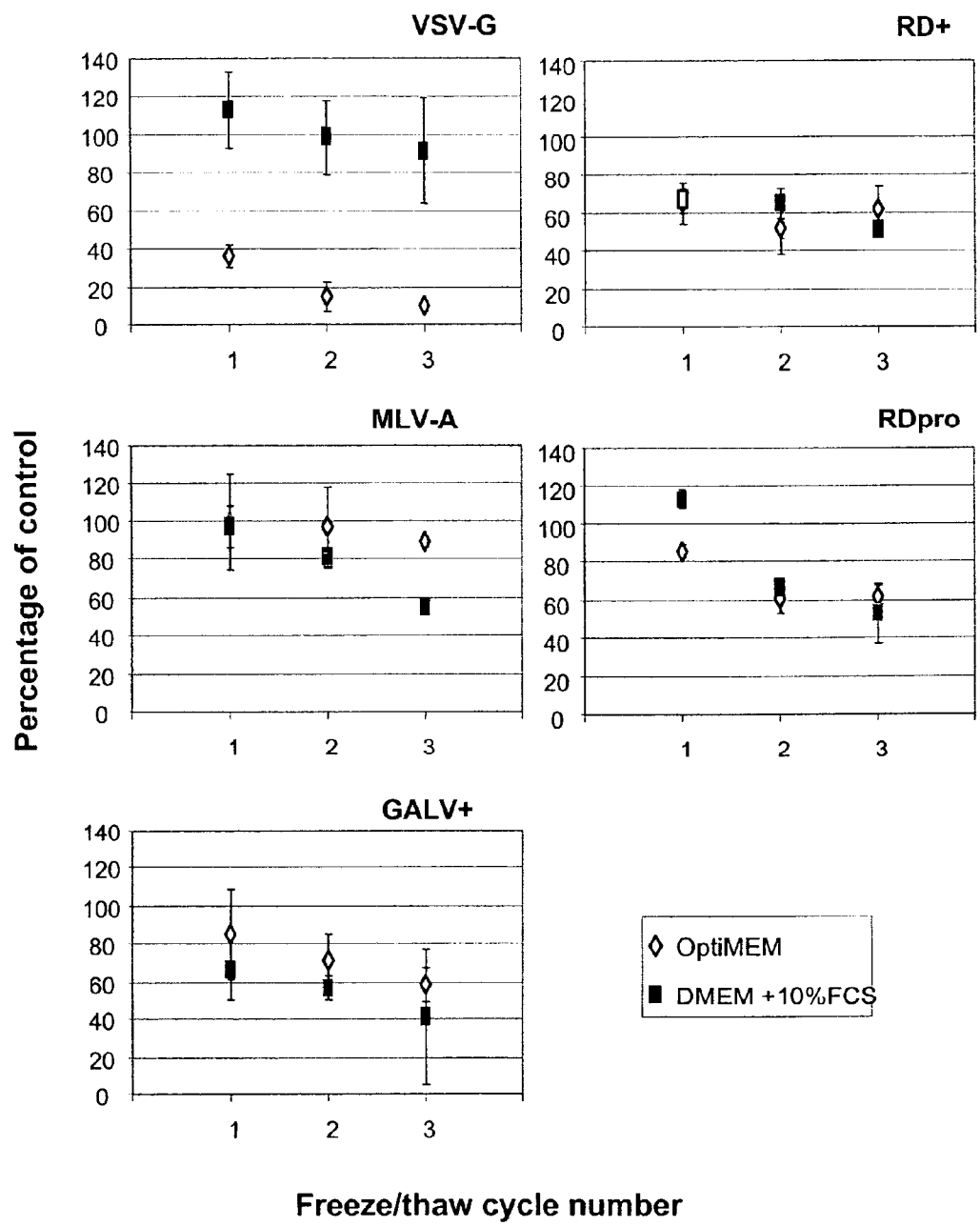
FIG. 15 shows graphs illustrating resistance of HIV-1 vectors to freeze/thaw cycling. Pseudotyped HIV vectors were frozen and thawed at −80° C. and 37° C., respectively, up to three times. Relative eGFP titre to the control titre before initiating the first cycle on 293T in the presence of 8 µg/ml polybrene is presented in percentages. Values shown are the mean of two experiments and the error bars indicate the actual data points.

Vector stability during freeze/thaw cycles was then examined by titrating virus onto 293 T cells after cycling between −80° C. and 37° C. The titre is presented as a percentage of titre before commencing the first cycle (FIG. 15). All gammaretrovirus pseudotypes showed some resistance to freeze/thaw. After one cycle the MLV-A pseudotyped vector lost less than 5% of its original titre in either media. All other retroviral pseudotypes appeared to be more sensitive to freeze/thaw, although after three cycles no retroviral pseudotype lost greater than 50% of its original titre. There was no substantial difference in stability between vectors harvested in OptiMEM and DMEM+10% FCS. This, however, was not the case for the HIV-1 (VSV-G) vector. After one cycle the virus harvested in OptiMEM lost up to 65% of its original titre, while virus titre in DMEM+10% FCS appeared to be stable. Moreover, after three cycles virus in OptiMEM lost 90% of its original titre while that in DMEM+10% FCS lost less than 10%. Thus the condition for freezing HIV-1 (VSV-G) may need careful optimisation.

Example 8

Resistance to Inactivation in Fresh Human Sera

Figure 16:
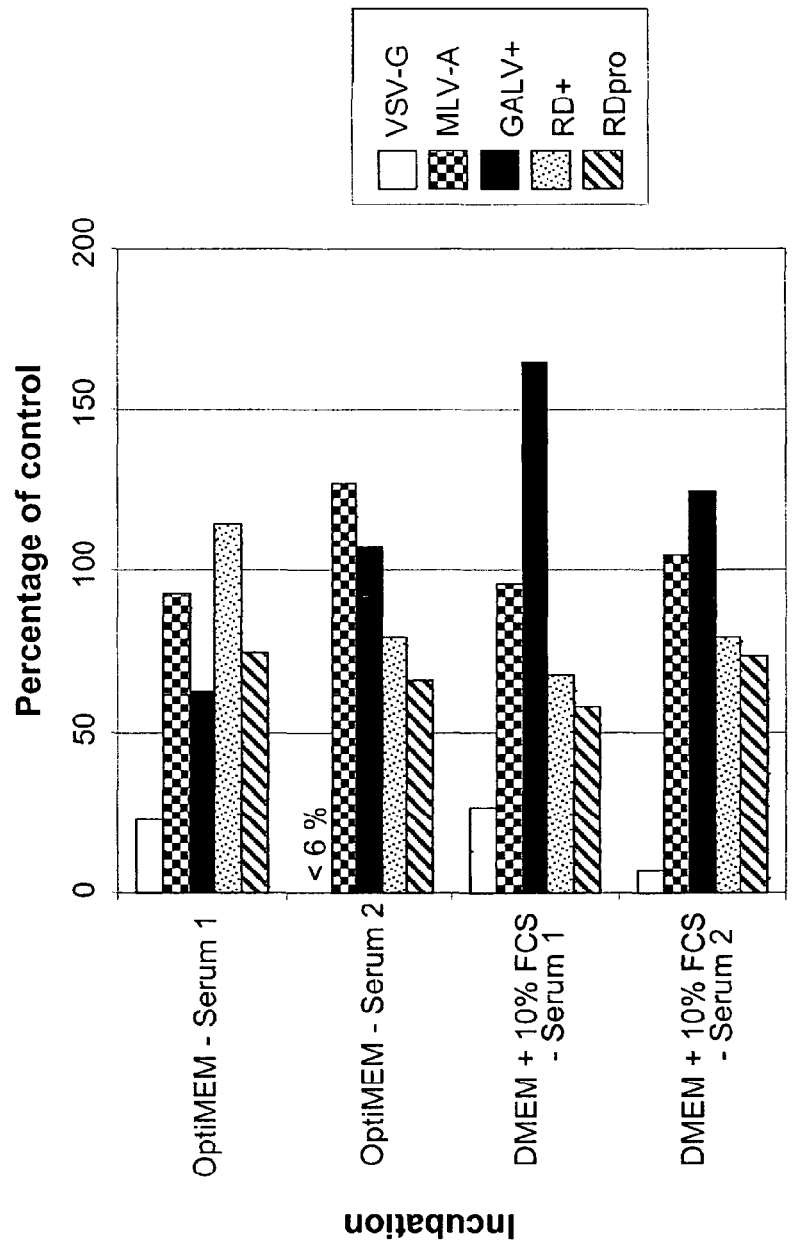
FIG. 16 is a graph showing resistance of HIV-1 vectors to human sera. Pseudotyped HIV vectors harvested in either OptiMEM or DMEM+10% FCS were exposed to human sera. Titre on 293 T cells in the presence of 8 µg/ml polybrene is represented as a percentage of the viral titre after incubation with fresh frozen serum in relation to incubation with corresponding heat inactivated serum. Values shown are the mean of two experiments. In the two experiments viral titre did not vary by greater than 2 fold. Values below 6% of the control titre could not be detected by FACS.

Each virus, in either OptiMEM or DMEM+10% FCS, was incubated at 37° C. for 1 hour with an equal volume of fresh or heat inactivated sera and then titrated on 293 T cells. A percentage of the viral titre after incubation with fresh frozen serum in relation to incubation with the corresponding heat inactivated serum is shown (FIG. 16). All gammaretroviral pseudotypes in both media exhibited good stability when exposed to human sera. HIV-1 (MLV-A) lost at most 8% of titre while those bearing the GALV+ envelope showed a loss of titre (27%) in one instance. The highest reduction in retroviral pseudotype titre HIV-1 (RDpro) harvested in DMEM+10% FCS exposed to Sera 1 is no greater than 40%. HIV-1 (VSV-G) virus, in contrast, appeared to be sensitive to inactivation by fresh human sera. There was no substantial difference in serum sensitivity between vectors with different gammaretrovirus env in this study. In contrast, we previously reported that replication competent MLV-A was more sensitive than RD114 or GALV when produced by galactosyl(α1-3)galactosyl (αGal) negative human cells (Takeuchi Y et al. *Nature* 1996; 379: 85-88).

HIV-1 (VSV-G) was more sensitive to inactivation in fresh human serum than HIV-1 vectors pseudotyped with gammaretroviral Env. Exposure to Serum 1 causes a loss of up to 80% of titre, whereas incubation with Serum 2 caused a drop in titre of this virus to below the detection threshold. These results are consistent with data by DePolo (DePolo N J et al. *Mol Ther* 2000; 2: 218-222) and colleagues indicating that a VSV-G pseudotyped HIV vector is readily inactivated in human serum by complement (DePolo N J et al. Mol Ther 2000; 2: 218-222). Furthermore, our results and those of DePolo and co-workers are consistent with previous observations that wild type VSV replicating in human cells, devoid of the xenogeneic αGal antigen, were sensitive to inactivation in fresh human serum, although less so than VSV bearing αGal antigens (Takeuchi Y et al. *J Virol* 1997; 71: 6174-6178; Welsh R M, et al. *J Virol* 1998; 72: 4650-4656).

Example 9

Resistance to Inactivation in Fresh Human Sera

Figure 17:
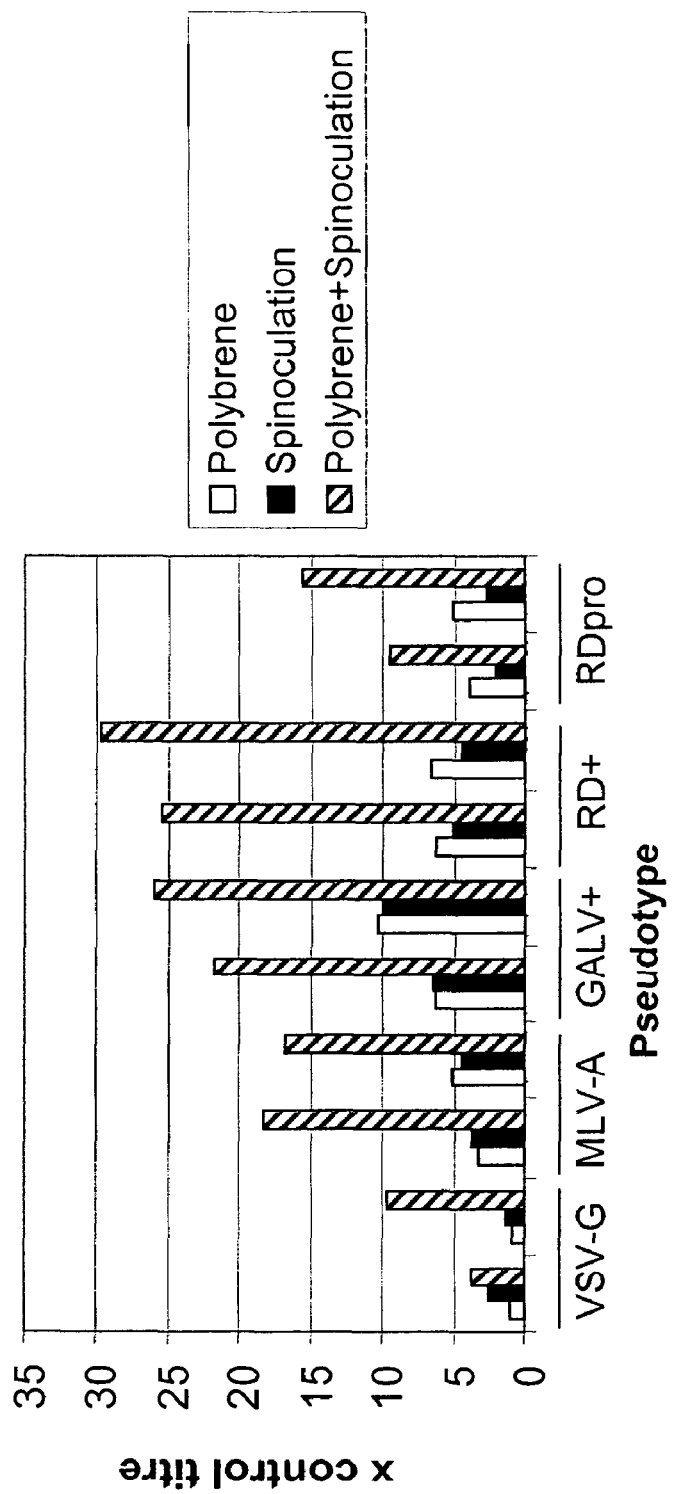
FIG. 17 is a graph showing the effect of polybrene and spinoculation on HIV-1 vector infection. HIV-1 vectors were harvested in OptiMEM. Each pseudotype was titrated on 293 T cells and spun down at 1200 g for 2 hours at 25° C. or titrated on 293T in the presence of polybrene (8 µg/ml) or both. Values of relative titre to control titre in the absence of polybrene and without spinoculation are shown.

Vector concentration before transduction or modification of the in vitro or ex vivo transduction procedure to augment virus binding is commonly performed to enhance titres of retro/lentivirus vector harvests. We investigated vector titre enhancement by the use of polybrene and centrifugal inoculation or spinoculation. Pseudotype vectors were harvested in OptiMEM. Each pseudotype was titrated onto 293 T cells in the presence of the polybrene, or the use of spinoculation or both. The results from these experiments are shown in FIG. 17. Polybrene enhanced infection of HIV-1 vectors with gammaretrovirus env on average 5-6×, whereas spinoculation enhanced infection on average 4×. The presence of polybrene did not substantially enhance HIV-1 (VSV-G) titre. When polybrene and spinoculation were used together their effect in all cases was additive.

The enhancement effect of polybrene on different cell lines (the human cell lines 293T, TE671, HeLa and HT1080 and the murine cell line NIH 3T3) was also investigated (data not shown). Polybrene did not raise HIV-1 (VSV-G) titre by greater than 2× on any cell line tested. The effect of polybrene on gammaretrovirus pseudotype titre was most notable on 293 T or TE671 cells (8×-16×), while its effect is less dramatic on HeLa or HT1080 cells (2×-4×). The infection enhancement of polybrene on NIH 3T3 cells was negligible.

Example 10

Concentration of STAR Cell Derived Pseudotypes

Figure 18:
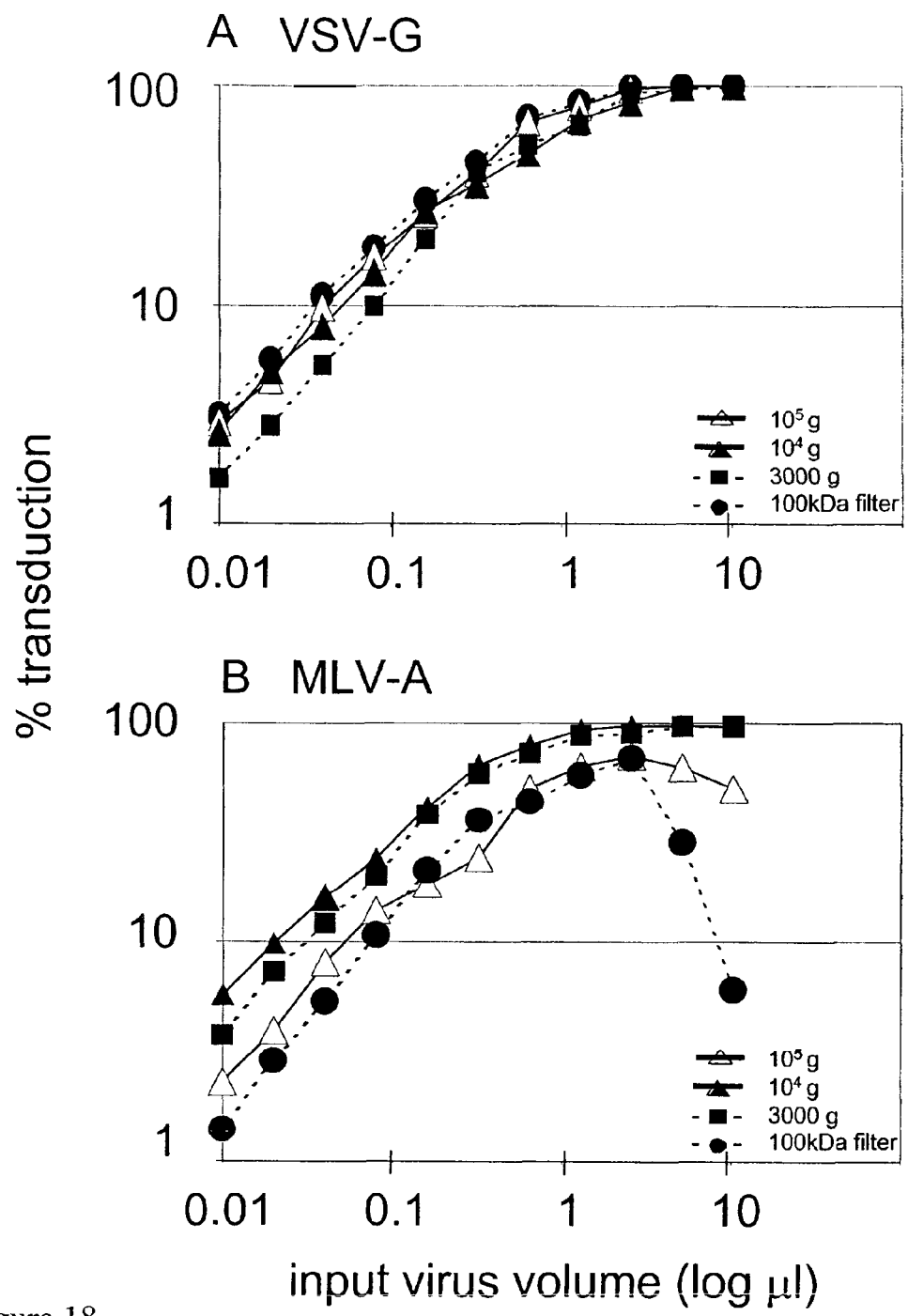
FIGS. 18A-18B show graphs illustrating titration of concentrated HIV-1 vectors. HIV-1 (MLV-A) (FIG. 18A) and HIV-1 (VSV-G) (FIG. 18B) harvested in OptiMEM were concentrated 40 fold by a range of methods; ultracentrifugation at 100,000 g and 10,000 g, low-speed centrifugation at 3,000 g and centrifugal filtration using Centricon-20 filters (100 kDa filter). Each concentrated stock was diluted in a 2-fold series and titrated onto 293 T cells in the presence of 8 µg/ml polybrene. eGFP transduced cells were counted by FACS.

Concentration of vector stocks is often necessary. Ultracentrifugation, low-speed centrifugation and centrifugal filtration (or ultrafiltration) have been applied for HIV-1 (VSV-G) vector concentration successfully (Naldini L et al. *Science* 1996; 272: 263-267; Reiser J. et al. *Gene Ther* 2000; 7: 910-913; VandenDriessche T, et al. *Methods Enzymol* 2002; 346: 573-589). With regard to gammaretrovirus pseudotypes, only HIV-1 (MLV-A) has been examined to gauge its ability to be concentrated by ultracentrifugation and centrifugal filtration. We, therefore, carried out a comparative study, concentrating the 4 different pseudotypes by 4 different methods/conditions. Vectors bearing MLV-A, GALV+ and RDpro env as well as VSV-G were harvested in OptiMEM and concentrated 40-fold in volume by four conditions—centrifugal filtration using a filter with a cut-off of 100 kDa or centrifugation at three different speeds: 100,000 g for 1.5 h; 10,000 g for 1.5 h; 3,000 g for 7 h. Before and after concentration % eGFP transduced cells was measured in 2-fold serial dilutions on 293 T cells in the presence of polybrene. FIG. 18 shows examples of the titration curves for HIV-1 (MLV-A) and HIV-1 (VSV-G). eGFP titre and % recovery of each vector preparation after the concentration procedure was estimated using % transduction data for dilutions in linear range of titration and shown in Table 1.

TABLE 1

Concentration of HIV-1 Vectors
eGFP titre (% recovery after concentration)
Centrifigation

| Envelope | Uncon-centrated | 105 g | 104 g | 3000 g | 100k DA filter[a] |
|---|---|---|---|---|---|
| VSV-G | 1.5[b] | 56 (92)[c] | 52 (85) | 28 (47) | 36 (60) |
| MLV-A | 2.1 | 40 (60) | 100 (117) | 72 (180) | 28 (32) |
| GALV+ | 0.5 | 11 (55) | 18 (90) | 9 (45) | 10 (50) |
| RDpro | 1.5 | 45 (75) | 136 (226) | 59 (98) | 13 (21) |

Virus produced was concentrated by concentrated 40 fold by centrifugation at 100,000 g, 10,000 g and 3,000 g and centrifugal filtration with 100 kDa cutoff (a). Virus was titrated on 293 T cells with 8 μg/ml polybrene and eGFP expression assayed by FACS. b, titre is expressed as $10^7$ iu/ml; c, % recovery (100× titre after concentration)/(40× unconcentrated titre) shown in parentheses.

Limited damage to vectors by concentration was observed, as vector recovery was more than 50% in most experiments. Centrifugation at 10,000 g or 3,000 g generally resulted in higher recovery for gammaretroviral pseudotypes. HIV-1 (VSV-G) may be more stable than HIV-1 vectors with gammaretrovirus env when concentrated at higher ultracentrifugation speeds or by centrifugal filtration. Also, in an extension of this study, it was noted that greater concentration, up to 100-fold, could be achieved with high yield by one step centrifugation at either 10,000 g or 3,000 g, resulting in the titre of $2.0 \times 10^8$ -$1.5 \times 10^9$ iu/ml (data not shown).

Whilst HIV-1 (VSV-G) achieved 100% infection at high doses after concentration in all conditions (FIG. 18Bb), gammaretroviral pseudotypes could achieve 100% infection on 293 T cells only when viral supernatant was subjected to milder conditions of centrifugation (FIG. 18Aa for HIV-1 (MLV-A), data not shown for HIV-1 (GALV+) and HIV-1 (RDpro)). At high doses, infection of gammaretrovirus pseudotypes was inhibited when virus particles were concentrated by either ultracentrifugation at a speed of 100,000 g or centrifugal filtration. It has been previously reported that an MLV vector packaging cell line, FLYA13 (Cosset, F-L., et al. *J. Virol.* 69, 7430-7436 (1995)), expels large quantities of MLV-A env free from vector particles into the culture media. Excess soluble env appeared to inhibit vector transduction, competing with vector particles for their cellular receptor (Slingsby J H et al. *Hum Gene Ther* 2000; 11: 1439-!451; Arai T et al. *J Virol* 1998; 72: 1115-1121). To determine if soluble MLV-A env was concentrated together with vector particles during centrifugal filtration, thereby causing reduced transduction by the filtrated preparation at high doses, the preparation by centrifugal filtration was fractionated by Sepharose gel filtration. Gel filtration fractions were analysed for infection and presence of HIV-1 capsid (CA) and MLV-A env (FIGS. 8A and 8B). eGFP infectivity and HIV-1 p24 were detected in early flow-through fractions, indicating presence of infectious vector particles. These flow-through fractions, 3-5, were capable of high rate transduction at high doses as 95-100% transduction was achieved by 20 μl input of fractions (data not shown) compared to about 5% by the preparation after centrifugal filtration before gel filtration (FIG. 19C). This indicates that gel filtration separated some inhibitors from vector particle fractions. Western blot probed with anti-MLV SU revealed that majority of MLV-A env SU appeared in later fractions 10-13, indicating that a large amount of particle-free env was present in centrifugal filtration preparation (FIG. 19B).

In order to test for inhibition of vector infection by late fractions free from vector particles, fractions 9-22 were plated on 293 T cells together with a fixed dose of HIV-1 (MLV-A) and HIV-1 (RDpro) (FIG. 19C). Without inhibition these vector doses resulted in 40-50% eGFP transduction. Substantial reduction of eGFP transduction by HIV-1 (MLV-A), but not HIV-1 (RDpro), was observed for fractions 10-13, which contain most MLV-A Env. This indicates that the non-virion associated envelope present in fractions 10-13 specifically inhibited HIV-1 (MLV-A) infection, presumably competing out vector particles for cellular receptors.

These results, therefore, suggest that non-virion associated envelope found in the supernatant of STAR cells producing gammaretrovirus pseudotypes can act as an inhibitor of infection when concentrated with viral particles. There does not, however, appear to be inhibition of infection at high dose when virus particles are concentrated at lower speeds. Centrifugation at the speeds between 10,000 g and 100,000 g could, therefore, be used in applications that require the preparation of concentrated virus stocks. Furthermore, low-speed centrifugation, albeit taking longer time, may be more suitable for concentrating large batches of vector stocks.

In summary, HIV vectors produced from STAR cells and pseudotyped with gammaretroviral env can infect certain types of human cells as efficiently as VSV-G pseudotyped HIV-1 vectors. They are more stable in fresh human serum and can be more effectively used with polybrene and spinoculation in ex vivo application than HIV-1 (VSV-G). They are resistant to freeze/thaw but their decay rate at 37° C. is faster than that of HIV-1 (VSV-G). This is potentially advantageous where local gene transfer without unwanted vector spread is required. Soluble env in vector preparation is preferably carried out using vector centrifugation. These results, along with the ease of quality control in stable, continuous vector production compared to that in transient or inducible systems, support further consideration of pre-clinical and clinical application of HIV-1 vectors from STAR cells pseudotyped with gammaretroviral Env.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

All publications and documents mentioned herein are incorporated herein by reference in their entirety, including all publications and documents referenced therein.

What is claimed is:

1. A method for producing a stable lentiviral packaging cell comprising transducing a cell with a retroviral vector comprising a nucleotide sequence encoding lentiviral Gag-Pol, wherein the retroviral vector is of different viral origin than a lentivirus, and wherein the lentiviral packaging cell stably produces lentiviral Gag-Pol continuously for at least 3 months.

2. The method of claim 1, wherein the lentiviral packaging cell is an HIV packaging cell.

3. The method of claim 1, wherein the retroviral vector is an MLV retroviral vector.

4. The method of claim 1, further comprising transfecting the cell with a nucleotide sequence encoding an envelope protein.

5. The method of claim 1, wherein the nucleotide sequence encoding lentiviral Gag-Pol is codon-optimized.

6. The method of claim 4, wherein the envelope protein is a gammaretrovirus envelope protein.

7. A stable lentiviral packaging cell, wherein the packaging cell comprises a retroviral vector comprising a nucleotide sequence encoding lentiviral Gag-Pol, wherein the retroviral vector is of different viral origin than a lentivirus, and wherein the lentiviral packaging cell stably produces lentiviral Gag-Pol continuously for at least 3 months.

8. The stable lentiviral packaging cell of claim 7, which is an HIV packaging cell.

9. The stable lentiviral packaging cell of claim 7, wherein the retroviral vector is an MLV retroviral vector.

10. The stable lentiviral packaging cell of claim 7, further comprising a nucleotide sequence encoding an envelope protein.

11. The stable lentiviral packaging cell of claim 7, wherein the nucleotide sequence encoding lentiviral Gag-Pol is codon-optimized.

12. A method of producing a lentiviral vector particle comprising introducing a lentiviral vector comprising a nucleotide sequence of interest (NOI) into the stable packaging cell of claim 7.

13. The stable lentiviral packaging cell of claim 10, wherein the envelope protein is a gammaretrovirus envelope protein.

14. A method of producing a lentiviral vector particle comprising introducing a lentiviral vector comprising a nucleotide sequence of interest (NOI) into the stable packaging cell of claim 10.

* * * * *

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Gag-pol detection primer F1

<400> SEQUENCE: 1
tgcatccagt gcatgcaggg cctat                                          25

<210> SEQ ID NO 2
<211> LENGTH: 26
<212> TYPE: DNA
<213> ORGANISM: Artificial Sequence
<220> FEATURE:
<223> OTHER INFORMATION: Gag-pol detection primer R1

<400> SEQUENCE: 2
tctttgccac aattgaaaca cttaac                                         26

<210> SEQ ID NO 3
<211> LENGTH: 26
<212> TYPE: DNA
<213> ORGANISM: Artificial Sequence
<220> FEATURE:
<223> OTHER INFORMATION: Gag-pol detection primer SynF1

<400> SEQUENCE: 3
ggtgcacgca gggcccatcg caccgg                                         26

<210> SEQ ID NO 4
<211> LENGTH: 26
<212> TYPE: DNA
<213> ORGANISM: Artificial Sequence
<220> FEATURE:
<223> OTHER INFORMATION: Gag-pol detection primer SynR1

<400> SEQUENCE: 4
gccacagttg aagcacttga cgatct                                         26

<210> SEQ ID NO 5
<211> LENGTH: 26
<212> TYPE: DNA
<213> ORGANISM: Artificial Sequence
<220> FEATURE:
<223> OTHER INFORMATION: Gag-pol detection primer F2

<400> SEQUENCE: 5 agggaagtg acatagcagg aactac                                          26

<210> SEQ ID NO 6
<211> LENGTH: 25
<212> TYPE: DNA
<213> ORGANISM: Artificial Sequence
<220> FEATURE:
<223> OTHER INFORMATION: Gag-pol detection primer R2

<400> SEQUENCE: 6
gcctttctgt atcattatgg tagct                                          25

<210> SEQ ID NO 7
<211> LENGTH: 27

```
<212> TYPE: DNA
<213> ORGANISM: Artificial Sequence
<220> FEATURE:
<223> OTHER INFORMATION: Gag-pol detection primer SynF2

<400> SEQUENCE: 7
acggggctca gacatcgccg gaacgac                                            27

<210> SEQ ID NO 8
<211> LENGTH: 26
<212> TYPE: DNA
<213> ORGANISM: Artificial Sequence
<220> FEATURE:
<223> OTHER INFORMATION: Gag-pol detection primer SynR2

<400> SEQUENCE: 8
aaagttgccg cgctgcatca tgatgg                                             26
```